(12) United States Patent
Takimoto et al.

(10) Patent No.: US 7,850,609 B2
(45) Date of Patent: Dec. 14, 2010

(54) ULTRASOUND DIAGNOSTIC APPARATUS

(75) Inventors: Masao Takimoto, Otawara (JP); Tomohisa Imamura, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 578 days.

(21) Appl. No.: 11/084,159

(22) Filed: Mar. 21, 2005

(65) Prior Publication Data

US 2005/0222506 A1 Oct. 6, 2005

(30) Foreign Application Priority Data

Mar. 24, 2004 (JP) ............................. 2004-086749
Mar. 4, 2005 (JP) ............................. 2005-061602

(51) Int. Cl.
*A61B 8/00* (2006.01)

(52) U.S. Cl. ...................... 600/437; 600/441; 600/443; 600/450

(58) Field of Classification Search ................. 600/441, 600/443, 450, 437
See application file for complete search history.

(56) References Cited

U.S. PATENT DOCUMENTS

| | | | |
|---|---|---|---|
| 5,477,858 A * | 12/1995 | Norris et al. ................. 600/441 |
| 5,485,844 A | 1/1996 | Uchibori | |
| 5,860,927 A * | 1/1999 | Sakaguchi et al. ........... 600/453 |
| 6,171,246 B1 * | 1/2001 | Averkiou et al. ............. 600/458 |
| 6,210,335 B1 * | 4/2001 | Miller ......................... 600/454 |
| 6,221,018 B1 * | 4/2001 | Ramamurthy et al. ....... 600/443 |
| 6,612,989 B1 * | 9/2003 | Brock-Fisher ............... 600/447 |
| 6,824,518 B2 * | 11/2004 | Von Behren et al. ........ 600/443 |

FOREIGN PATENT DOCUMENTS

| | | |
|---|---|---|
| JP | 6-327672 | 11/1994 |
| JP | 2001-149370 | * 6/2001 |
| JP | 2004-16241 | 1/2004 |

* cited by examiner

*Primary Examiner*—Long V Le
*Assistant Examiner*—Ellsworth Weatherby
(74) *Attorney, Agent, or Firm*—Oblon, Spivak, McClelland, Maier & Neustadt, L.L.P.

(57) ABSTRACT

An ultrasound diagnostic apparatus comprises an ultrasound probe having a plurality of piezoelectric transducers to transmit ultrasound waves to a subject and to receive echoes from the subject, a driving unit which generates a plurality of driving signals corresponding to the plurality of piezoelectric transducers to generate the ultrasound waves therefrom, a Doppler signal detecting unit which detects Doppler signals based on the echoes, a spectrum data generating unit which generates spectrum data based on the detected Doppler signals, and a display unit which displays the spectrum data. The ultrasound diagnostic apparatus further comprises a controller which controls the driving unit to switch, in synchronization with a biomedical signal of the subject, a high-power mode in which amplitude of the driving signal is relatively high and a low-power mode in which amplitude of the driving signal is relatively low.

7 Claims, 17 Drawing Sheets

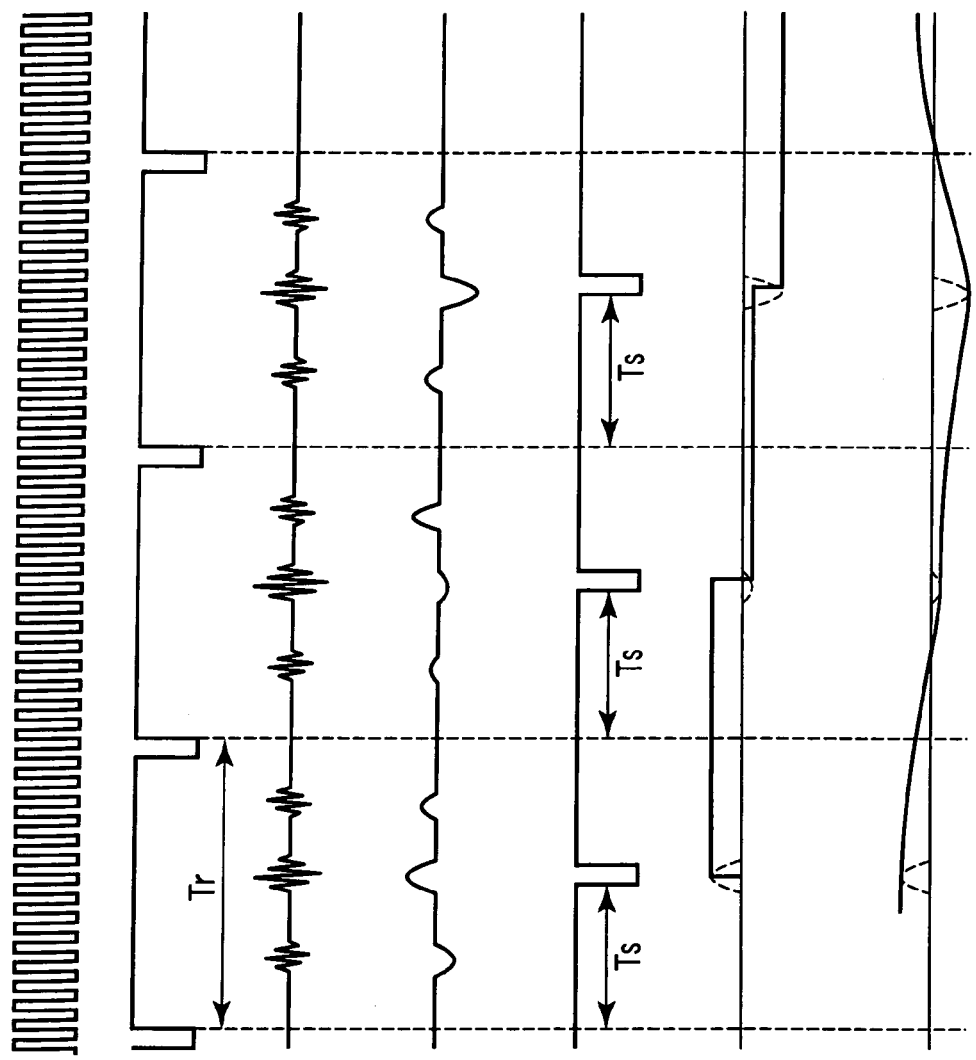
FIG. 3A Reference signal
FIG. 3B Rate pulse
FIG. 3C Reception signal
FIG. 3D Quadrature-phase-detection output
FIG. 3E Sampling pulse
FIG. 3F Doppler signal (SH output)
FIG. 3G Doppler signal (HPF output)

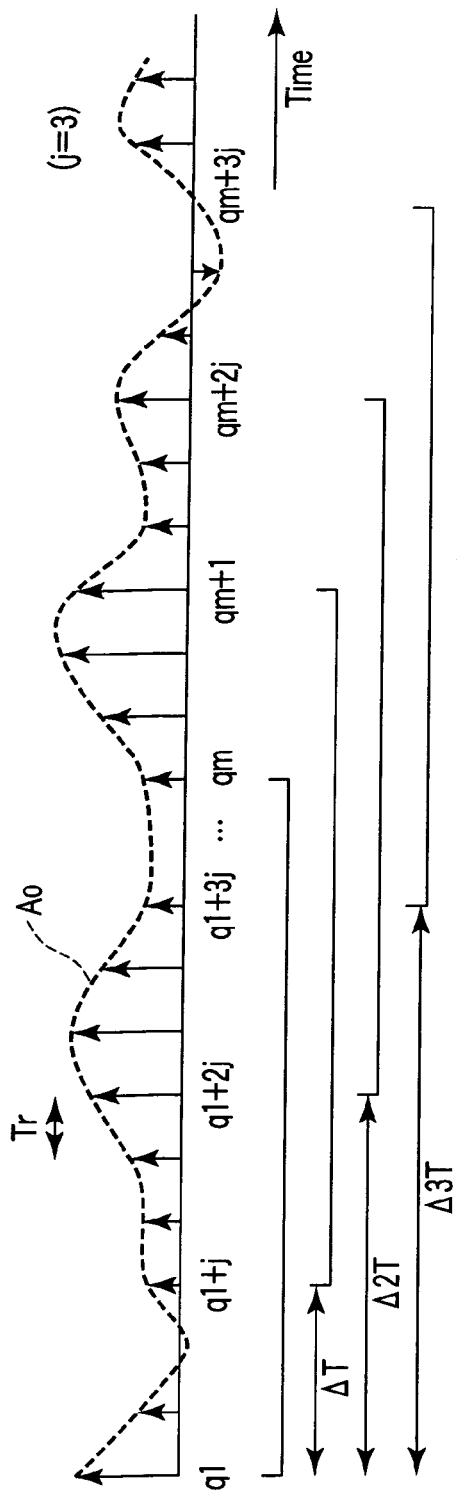
F I G. 4A
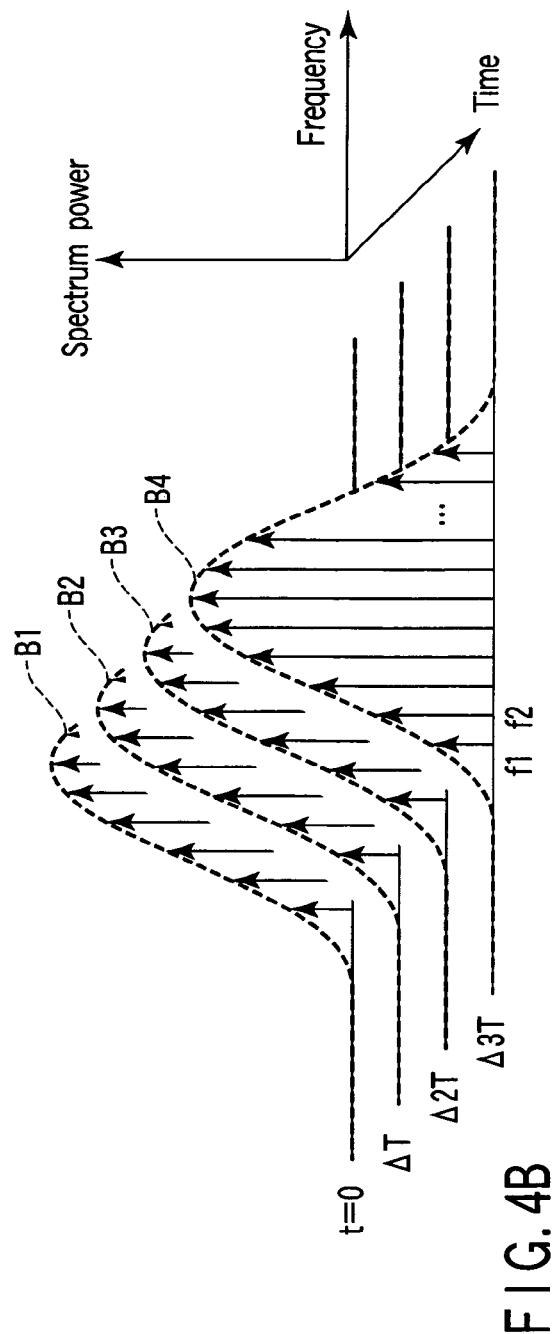
F I G. 4B

|  | Normal mode | High power mode | Low power mode |
|---|---|---|---|
| Pulse doppler method | — | $V_H$ | $V_L$ |
| B-mode method | $V_{BH}$ | — | $V_{BL}$ |
| Color doppler method | $V_{CH}$ | — | $V_{CL}$ |

FIG. 8

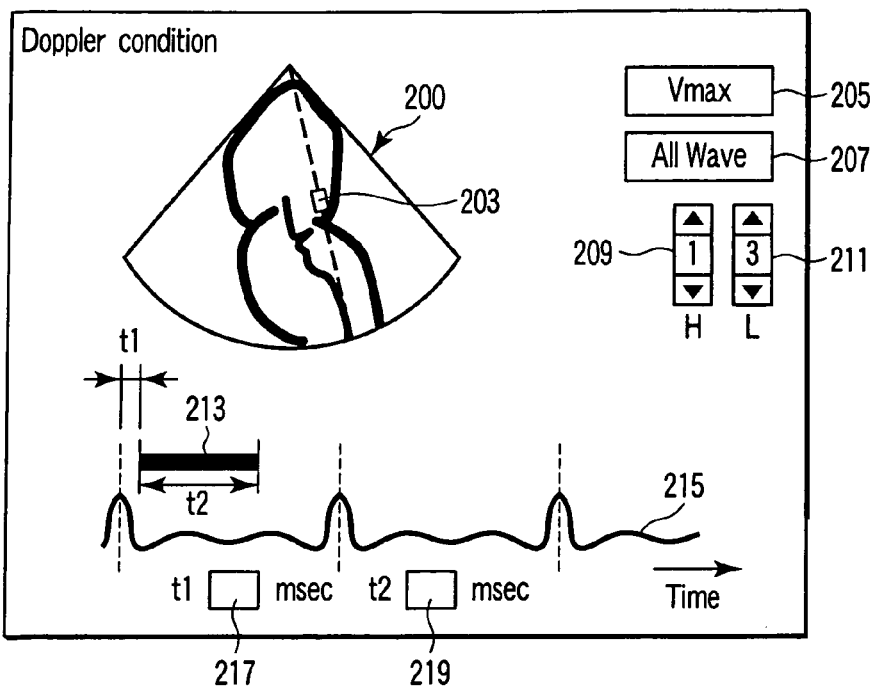
F I G. 17
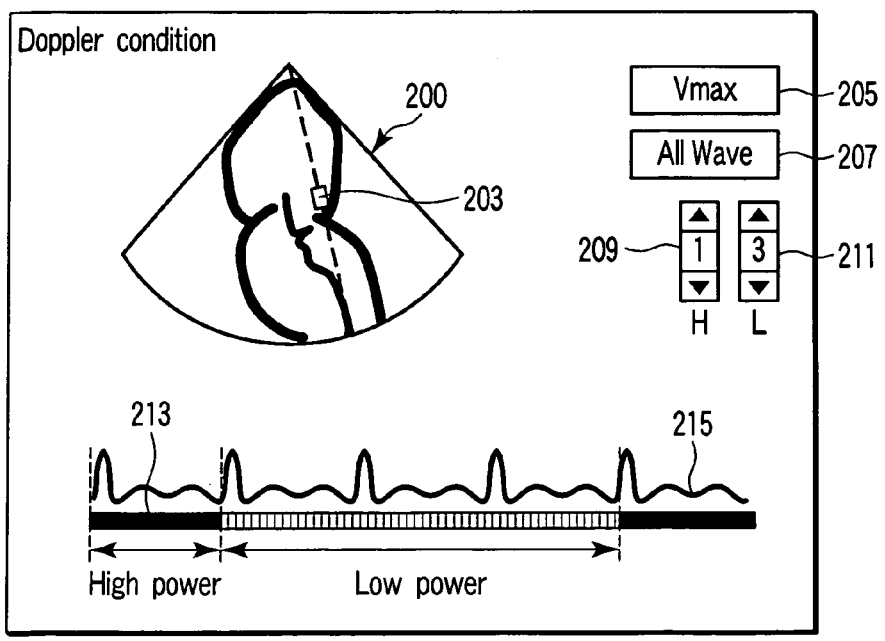
F I G. 18

ULTRASOUND DIAGNOSTIC APPARATUS

CROSS-REFERENCE TO RELATED APPLICATIONS

This application is based upon and claims the benefit of priority from prior Japanese Patent Applications No. 2004-086749, filed Mar. 24, 2004; and No. 2005-061602, filed Mar. 4, 2005, the entire contents of both of which are incorporated herein by reference.

BACKGROUND OF THE INVENTION

1. Field of the Invention

The present invention relates to an ultrasound diagnostic apparatus, and more particularly to an ultrasound diagnostic apparatus for displaying spectrum data of a Doppler signal obtained by transmitting/ receiving an ultrasound wave to/from an object and performing various measurements based on the spectrum data.

2. Description of the Related Art

The ultrasound diagnostic apparatus emits an ultrasound pulse or a continuous wave generated from a piezoelectric transducer incorporated in an ultrasound probe into the subject(patient), and receiving an ultrasound reflected wave generated by a difference in acoustic impedance between subject tissues and displaying it on a monitor. This diagnostic method is classified into ultrasound tomography for displaying a two-dimensional image by using an ultrasound pulse, and a so-called ultrasound Doppler spectrum method for displaying a time dependent change of a Doppler spectrum (referred to as spectrum data, hereinafter) obtained by frequency-analyzing a Doppler deviation component generated when an ultrasound pulse or an ultrasound continuous wave is applied to a moving reflector (e.g., blood or tissue) in the subject.

The ultrasound tomography includes a B-mode method for displaying a two-dimensional distribution of reflection intensity, and a color Doppler method for two-dimensionally displaying speed information of a blood flow or a tissue in color by using a Doppler component. These methods have widely been used for diagnosing patterns and functions of various organs since a two-dimensional image can be easily observed in real time by a simple operation of only bringing the ultrasound probe into contact with a body surface.

The ultrasound Doppler spectrum method includes a method for using a pulse wave (pulse Doppler method) and a method for using a continuous wave (continuous wave Doppler method) as in the case of the ultrasound tomography, both of which are used for quantitatively measuring a moving speed of a blood flow or a tissue. Especially, the pulse Doppler method is applied to a case in which resolution of a distance direction (ultrasound transmitting/receiving direction) is necessary and a flow velocity or a moving speed is relatively slow, and the continuous wave Doppler method is applied to a case in which a blood flow velocity is extremely fast and a Doppler spectrum is folded many times as in the case of a cardiac valve defect patient.

The spectrum data in the ultrasound spectrum method is usually displayed in a sonogram form in which an abscissa of a display screen corresponds to a time axis, an ordinate to a frequency component, and luminance to a size of power of each frequency component. For severity determination of the cardiac valve defect patient or the like, a maximum frequency component value (maximum flow velocity value) of a reverse-flow component spectrum displayed in the sonogram form or a tracing waveform generated based on the maximum frequency component of this spectrum is generally used.

FIGS. 16A to 16C show a conventional spectrum data generating method: FIG. 16A showing a Doppler spectrum 151 obtained by subjecting an ultrasound Doppler signal obtained from a subject by the pulse Doppler method or the continuous wave Doppler method to high-speed Fourier transformation (FFT) analysis, in which an ordinate corresponds to a Doppler deviation frequency and an abscissa corresponds to a size (power) of a spectrum, FIG. 16B spectrum data 152 indicating a time dependent change of the Doppler spectrum 151, in which an ordinate corresponds to a Doppler deviation frequency, an abscissa corresponds to an observation time, power of the Doppler spectrum 151 is represented by luminance, and an electrocardiographic wave (ECG wave) 153 collected with the spectrum data 152 is simultaneously displayed, and FIG. 16C a time dependent change of a size of an ultrasound wave (transmitted acoustic power, hereinafter) emitted from the piezoelectric transducer in the collection of the spectrum data. Conventionally, always constant transmitted acoustic power has been used as shown in FIG. 16C.

Meanwhile, it has conventionally been known that when an ultrasound wave emitted to the subject is reflected on the moving reflector, random interferences occur between reflected waves, resulting in interference noises (speckle noises) in the Doppler spectrum. That is, as shown in FIG. 16A, irregularities occur in the calculated Doppler spectrum 151 (solid line). Accordingly, discontinuous patterns also occur in the spectrum data 152 of FIG. 16B showing the time dependent change of the Doppler spectrum 151, causing a difficulty of accurately observing a time dependent change of a maximum frequency component (maximum flow velocity value) or the like.

The influence of the interference noises is conspicuous when an S/N ratio of the Doppler spectrum is small because reflection intensity from the moving reflector is small. For example, in the case of determining the severity of the cardiac valve defect patient or the like by tracing 155 of a maximum negative frequency component in the spectrum data, not only accurate automatic or manual tracing is difficult but also much time is necessary for tracing in the case of manual tracing, creating problems such as an increase in the load of a tracing operator and the like.

To deal with the problems, there has been proposed a method of reducing the interference noises by averaging movements in an observation time direction by frequency component units of the spectrum data (e.g., pp. 4 to 6, FIGS. 1 and 2, Jpn. Pat. Appln. KOKAI Publication No. 6-327672).

According to the method described in the Jpn. Pat. Appln. KOKAI Publication No. 6-327672, the influence of the interference noises is reduced, and thus a peripheral portion in the spectrum data, i.e., a maximum frequency component or the like, can be continuously and smoothly displayed, improving visibility of tracing data. However, to obtain such an effect, the movement averaging process must be carried out for a relatively long observation time. As a result, clearness of the spectrum data is greatly reduced.

Furthermore, as a method of improving the S/N ratio of the ultrasound Doppler signal, a method of increasing the transmitted acoustic power of the ultrasound probe is available. However, there are limits imposed by heat generation regulations or acoustic power regulations established by Food and Drug Administration (FDA) or the like. Especially, an upper limit is imposed on the transmitted acoustic power by regulations regarding a surface temperature of the ultrasound probe or a temperature increase of a biomedical tissue (so-called thermal index). In a normal apparatus, spectrum data is generated by using transmitted acoustic power near an upper limit of a permissible value. Thus, it is impossible to further increase the transmitted acoustic power.

BRIEF SUMMARY OF THE INVENTION

It is an object of the present invention to provide an ultrasound diagnostic apparatus capable of complying with heat generation regulations or acoustic power regulations by controlling a driving method of a piezoelectric transducer in an ultrasound Doppler spectrum method, and observing a target portion of a Doppler spectrum or spectrum data generated based on an ultrasound Doppler component obtained from a subject.

According to a first aspect of the present invention, there is provided an ultrasound diagnostic apparatus comprising an ultrasound probe having a plurality of piezoelectric transducers to transmit ultrasound waves to a subject and to receive echoes from the subject; a driving unit which generates a plurality of driving signals corresponding to the plurality of piezoelectric transducers to generate the ultrasound waves therefrom; a controller which controls the driving unit to switch, in synchronization with a biomedical signal of the subject, a high-power mode in which amplitude of the driving signal is relatively high and a low-power mode in which amplitude of the driving signal is relatively low; a Doppler signal detecting unit which detects Doppler signals based on the echoes; a spectrum data generating unit which generates spectrum data based on the detected Doppler signals; and a display unit which displays the spectrum data.

According to a second aspect of the present invention, there is provided an ultrasound diagnostic apparatus comprising an ultrasound probe having a plurality of piezoelectric transducers to transmit ultrasound waves to a subject and to receive echoes from the subject; a driving unit which generates a plurality of driving signals corresponding to the plurality of piezoelectric transducers to scan the inside of the subject with the ultrasound waves; a controller which controls the driving unit to switch, in synchronization with a biomedical signal of the subject, a high-power mode in which amplitude of the driving signal is relatively high and a low-power mode in which amplitude of the driving signal is relatively low; a data image generating unit which generates image data based on the echoes; and a display unit which displays the image data.

Additional subjects and advantages of the invention will be set forth in the description which follows, and in part will be obvious from the description, or may be learned by practice of the invention. The subjects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 3A to 3G are time charts showing basic operations of a Doppler signal detecting unit and a Doppler spectrum generating unit of the first embodiment;

FIGS. 4A and 4B are graphs showing an FFT analysis method of the first embodiment;

FIG. 8 is a table showing driving voltage setting in high-power and low-power modes of the first embodiment;

FIG. 17 is a graph showing a setting screen example of a high-power mode continuance period according to the first embodiment; and FIG. 18 is a graph showing another setting screen example of a high-power mode continuance period according to the first embodiment.

DETAILED DESCRIPTION OF THE INVENTION

Hereinafter, the embodiments of the present invention will be described with reference to the accompanying drawings.

First Embodiment

A feature of a first embodiment of the present invention described below is that spectrum data are collected by alternately repeating high-power mode driving for the purpose of collecting diagnostic information and low-power mode driving for the purpose of monitoring an apparatus operation or the like, and the high-power mode driving is started based on a biomedical signal of a subject.

(Apparatus Configuration)

Figure 1:
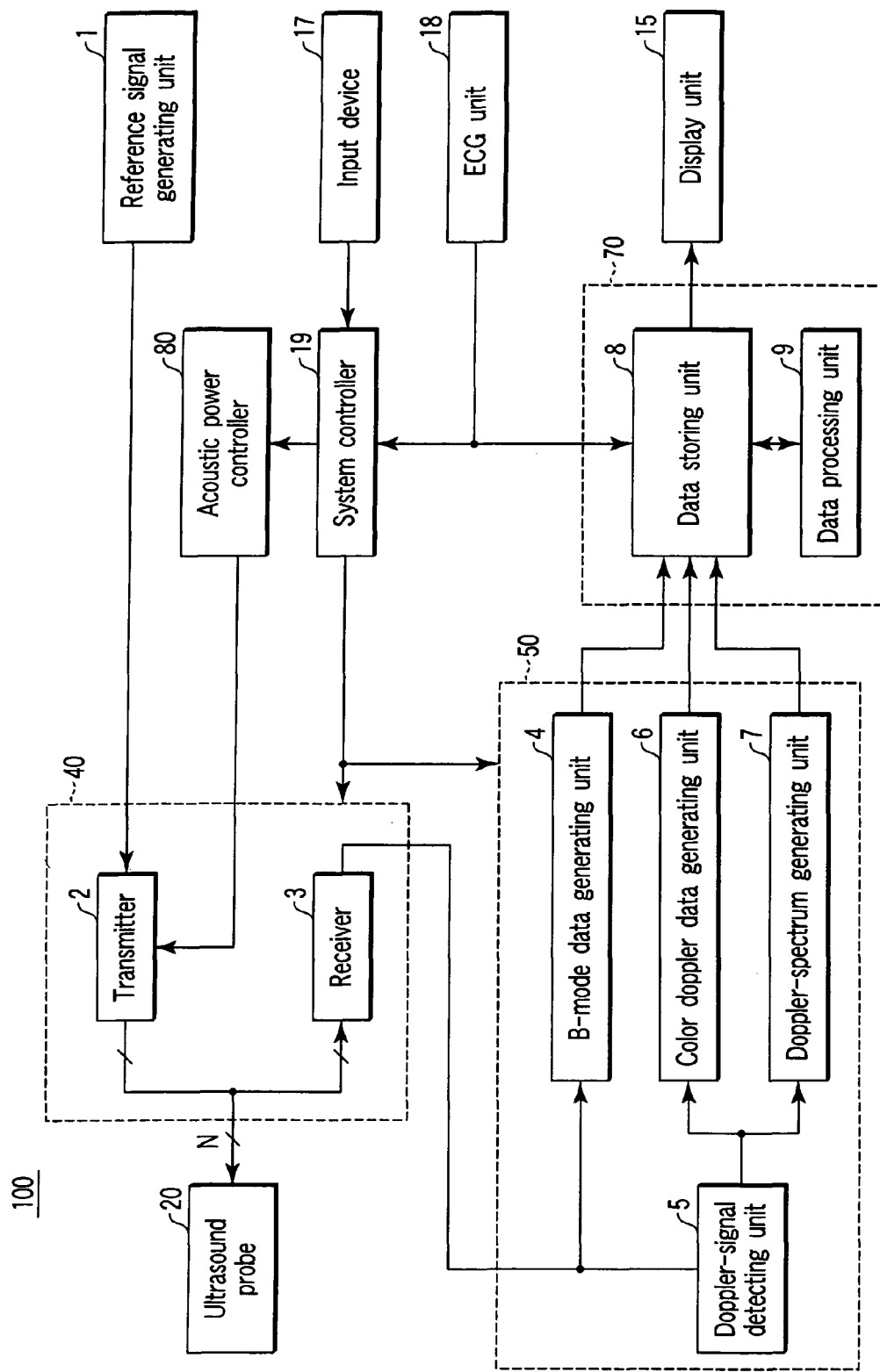
FIG. 1 is a block diagram showing an entire configuration of an ultrasound diagnostic apparatus according a first embodiment of the present invention.

Hereinafter, a configuration of an ultrasound diagnostic apparatus and an operation of each unit in the embodiment of the invention will be described with reference to FIGS. 1 to 6B. FIG. 1 is a block diagram showing an entire configuration of the ultrasound diagnostic apparatus of the embodiment, and FIG. 2 a block diagram showing a transmitting/receiving unit and a data generating unit which constitute the ultrasound diagnostic apparatus.

An ultrasound diagnostic apparatus 100 shown in FIG. 1 comprises an ultrasound probe 20 for transmitting/receiving an ultrasound wave for a subject, a transmitting/receiving unit 40 for transmitting/receiving an electric signal to/from the ultrasound probe 20, a data generating unit 50 for generating B-mode data, color Doppler data and Doppler spectrum data by processing the signal received from the transmitting/receiving unit 40, a data processing/storing unit 70 for saving the data generated by the data generating unit 50, generating two-dimensional B-mode image data, color Doppler image data, and spectrum data, and generating and saving cine-data by using the spectrum data, and a display unit 15 for displaying the B-mode image data, the color Doppler data, and the spectrum data which have been generated.

The ultrasound diagnostic apparatus 100 further comprises an acoustic power controller 80 for controlling transmitted acoustic power in ultrasound tomography or an ultrasound Doppler spectrum method, a reference signal generating unit 1 for generating a continuous wave or a rectangular wave of a frequency almost equal to a center frequency of an ultrasound pulse or a frequency (fo) of an ultrasound continuous wave to the transmitting/receiving unit 40 or the data generating unit 50, an input device 17 to which subject information, setting conditions, command signals and the like are input by an operator, and a system controller 19 for controlling the units of the ultrasound diagnostic apparatus 100 overall. An ECG unit 18 is separately disposed for collecting electrocardiographic waves of the subject.

The ultrasound probe 20 transmits/receives an ultrasound wave by bringing its front face into contact with a surface of the subject, and has a plurality (N pieces) of very small piezoelectric transducers one-dimensionally arrayed in its tip. This piezoelectric transducer is an electric acoustic conversion element which has a function of converting an electric pulse or a continuous wave into a transmitted ultrasound wave during transmission, and converting a ultrasound reflected wave (received ultrasound wave) into an electric signal (received signal) during reception. The ultrasound probe 20 constructed compact and lightweight is connected through a cable to the transmitting/receiving unit 40. The ultrasound probe 20 has sector scanning compatibility, linear scanning compatibility, convex scanning compatibility and the like, and these are optionally selected in accordance with portions to be diagnosed. Hereinafter, a case of using the sector scanning compatible ultrasound probe 20 for the purpose of diagnosing a cardiac patient will be described. However, a method is not limited to this, and the ultrasound probe 20 may be linear scanning compatible or convex scanning compatible.

Figure 2:
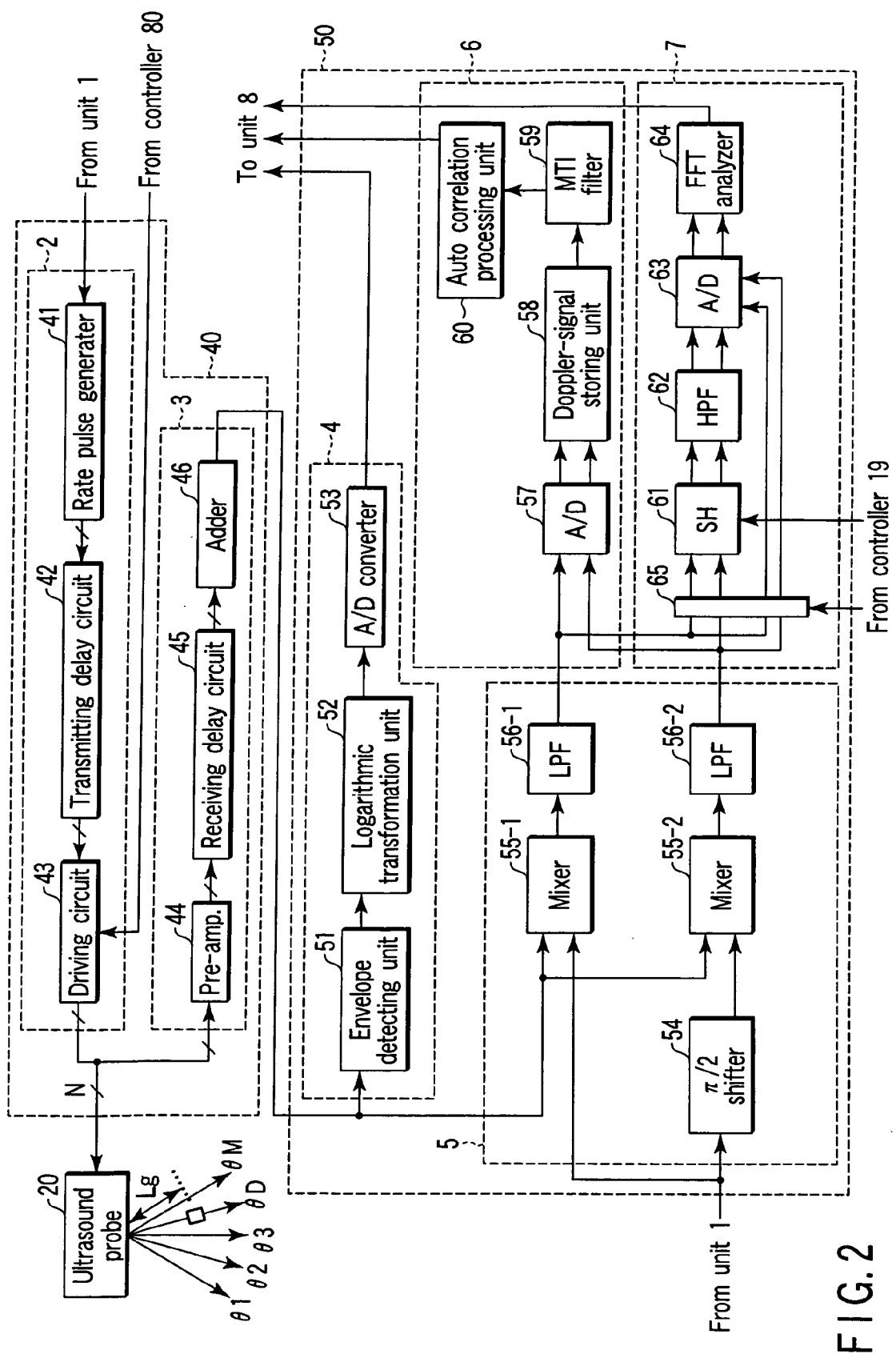
FIG. 2 is a block diagram showing configurations of a transmitting/receiving unit and a data generating unit of the first embodiment.

The transmitting/receiving unit 40 shown in FIG. 2 comprises a transmitter 2 for generating a driving signal to emit a transmitted ultrasound wave from the ultrasound probe 20, and a receiver 3 for receiving a received ultrasound wave from the ultrasound probe 20.

The transmitter 20 comprises a rate pulse generator 41, a transmitting delay circuit 42, and a driving circuit 4. The rate pulse generator 41 generates a rate pulse for deciding a repeating cycle (Tr) of a transmitted ultrasound wave by frequency-dividing a continuous wave fed from the reference signal generating unit 1 in a B-mode method, a color Doppler method or a pulse Doppler method. On the other hand, in a continuous wave Doppler method, the continuous wave fed from the reference signal generating unit 1 is directly fed to the transmitting delay circuit 42 of a next stage.

The transmitting delay circuit 42 gives a delay time for converging the transmitted ultrasound wave to a predetermined depth to obtain a thin beam width during transmission and a delay time for emitting the transmitted ultrasound wave in a predetermined direction to the rate pulse or the continuous wave fed from the rate pulse generator 41. The driving circuit 43 generates a driving signal for driving the piezoelectric transducer incorporated in the ultrasound probe 20 based on the rate pulse or the continuous wave. This driving circuit 43 generates normal and low-power mode driving signals in the B-mode method or the color Doppler method, or high-power mode and low-power mode driving signals in the ultrasound Doppler spectrum method based on a control signal fed from the acoustic power controller 80.

The receiver 3 comprises a preamplifier 44, a receiving delay circuit 45, and an adder 46. The preamplifier 44 amplifies a very small signal converted into an electric signal (received signal) by the piezoelectric transducer to secure a sufficient S/N ratio. The receiving delay circuit 45 gives a delay time for converging a received ultrasound wave from a predetermined depth to obtain a thin received beam width and a delay time for setting strong receiving directivity for a received ultrasound wave from a predetermined direction to an output of the preamplifier 44. Then, the output of the receiving delay circuit 45 to which the predetermined delay times have been given is sent to the adder 46 to be added and synthesized (phasing addition).

The transmitting delay circuit 42 and the driving circuit 43 in the transmitter 2 and the preamplifier 44 and the receiving delay circuit 45 in the receiver 3 usually have numbers of independent channels roughly equal to the number of piezoelectric transducers of the ultrasound probe 20. In the continuous wave Doppler method, a first piezoelectric transducer group obtained by dividing the N pieces of piezoelectric transducers into two, and the transmitter 2 connected to the first piezoelectric transducer group are used for transmitting waves, and the remaining second piezoelectric transducer group and the receiver 3 connected to thereto are used for receiving waves.

Next, the data generating unit 50 comprises a B-mode data generating unit 4 for receiving the received signal output from the added 46 of the receiver 3 to generate a B-mode data, a Doppler signal generating unit 5 for subjecting the received signal to quadrature detection to detect a Doppler signal, a color Doppler data generating unit 6 for processing the detected Doppler signal to generate color Doppler data, and a Doppler spectrum generating unit 7 for frequency-analyzing the Doppler signal to generate a Doppler spectrum.

In the high-power mode, a power value of the Doppler spectrum is high, thereby increasing display luminance typically. In the low-power mode, a power value of the Doppler spectrum is low, thereby reducing display luminance typically. Luminance varies between the high-power mode and the low-power mode. An S/N ratio varies between the high-power mode and the low-power mode. Spectrum waves (power frequency distribution) are essentially similar between the high-power mode and the low-power mode.

The B-mode data generating unit 4 comprises an envelope detecting unit 51, a logarithmic transformation unit 52, and an A/D converter 53. The envelope detecting unit 51 performs envelope detection for an input signal of the B-mode data generating unit 4, i.e., the received signal output from the adder 46 of the receiver 3, and the logarithmic transformation unit 52 performs logarithmic transformation for amplitude of the detected signal to relatively emphasize a weak signal. Then, the A/D converter 53 converts an output signal of the logarithmic transformation unit 52 into a digital signal to generate B-mode data.

The Doppler signal detecting unit 5 comprises a $\pi/2$ shifter 54, mixers 55-1 and 55-2, low-pass filters (LPF) 56-1 and 56-2, and performs quadrature phase detection for the received signal fed from the receiver 3 of the transmitting/receiving unit 40 by an operation (described later) to detect a Doppler signal.

The color Doppler data generating unit 6 comprises an A/D converter 57 of two channels, a Doppler signal storing unit 58, an MTI filter 59, an auto correlation processing unit 60. The A/D converter 57 converts the Doppler signals output from the LPF's 56-1 and 56-2 of the Doppler signal detecting unit 5, i.e., analog signal subjected to quadrature phase detection, into digital signals, and save the signals in the Doppler signal storing unit 58. Next, the MTI filter 59 which is a high-pass digital filter reads the Doppler signal temporarily stored in the Doppler signal storing unit 58, and removes a Doppler component (cluttering component) caused by a respiratory movement or a pulsating movement of an organ from the Doppler signal. The auto correlation processing unit 60 calculates an auto correlation value for the Doppler signal whose blood flow information alone is extracted by the MTI filter 59, and further calculates an average flow velocity value or a distribution value of the blood flow based on the auto correlation value.

The Doppler spectrum generating unit 7 comprises a switching circuit 65, a sample holding circuit (SH) 61, a high-pass filter (HPF) 62, an A/D converter 63, and an FFT analyzer 64. It is to be noted that the SH 61, the HPF 62, and the A/D converter 63 are all constituted of two channels, and complex components, i.e., a real component (I component) and an imaginary component (Q component), of the Doppler signal output from the Doppler signal detecting unit 5 are fed to each channel.

Next, basic operations of the Doppler signal detecting unit 5 and the Doppler spectrum generating unit 7 which are important components in the generation of the spectrum data in the embodiment will be described more in detail by referring to time charts of FIGS. 3A to 3G.

FIGS. 3A to 3G are time charts of spectrum data generation by the pulse Doppler method: FIG. 3A showing a reference signal output from the reference signal generating unit 1, FIG. 3B a rate pulse of a cycle Tr output from the rate pulse generator 41 of the transmitting/receiving unit 40, FIG. 3C a received signal obtained from the adder 46 of the receiver 3, FIG. 3D a quadrature phase detection output from the LPF 56 of the Doppler signal detecting unit 5, FIG. 3E a sampling pulse fed to the system controller 19 for deciding a sampling (range gate) of the SH 61 in the Doppler spectrum generating unit 7, FIG. 3F a Doppler signal sample-held by the SH 61, and FIG. 3G a Doppler signal smoothed through the HPF 62 in the range gate.

That is, the received signal (FIG. 3C) output from the receiver of FIG. 2 is input to a first input terminal of the mixers 55-1 and 55-2 of the Doppler signal detecting unit 5. On the other hand, the reference signal (FIG. 3A) of the reference signal generating unit 1 having a frequency fo almost equal to a center frequency of the received signal is directly fed to a second input terminal of the mixer 55-1, and the reference signal shifted by 90° in phase by the π/d shifter 54 is sent to the second input terminal of the mixer 55-2. Then, a multiplied output of the mixers 55-1 and 55-2 is sent to the LPF's 56-1 and 56-2, a component of a sum of the frequency of the input signal of the Doppler signal detecting unit 5 and the frequency (fo) of the reference signal fed from the reference signal generating unit 1 (component near 2 fo) is removed, and a difference component (component near 0 frequency) alone is extracted as a Doppler signal (FIG. 3D).

Next, the Doppler signal output from the LPF's 56-1 and 56-2, and a sampling pulse (range gate pulse) which the system controller 19 has generated by frequency-dividing the reference signal of the reference signal generating unit 1 are fed to the SH 61 (FIG. 3E), and the Doppler signal from a desired distance is sample-held based on the sampling pulse (FIG. 3F). It is to be noted that the sampling pulse is generated after a delay time Ts from the rate pulse (FIG. 3B) for deciding timing of emitting a transmitted ultrasound wave, and this delay time Ts can be optionally set in the input unit 17.

That is, the operator can extract the Doppler signal at a desired distance Lg from the ultrasound probe 20 by changing the delay time Ts of the sampling pulse. In this case, the following relation is set between the delay time Ts and the desired distance Lg, C indicating a sound velocity in the subject:

$$2LG/C = Ts$$

Next, a stepped noise component superimposed on the Doppler signal of the desired distance Lg output from the SH 61 is removed through the HPF 62 (FIG. 3G). The smoothed Doppler signal is converted into a digital signal by the A/D converter 63, and then fed to the FFT analyzer 64.

The FFT analyzer 64 comprises a processing circuit and a storing circuit (not shown). The Doppler signal output from the A/D converter 63 is temporarily stored in the storing circuit. The processing circuit performs FFT analysis in a predetermined period of a series of Doppler signals stored in the storing circuit.

On the other hand, in the case of the continuous wave Doppler method, an output of the Doppler signal detecting unit 5 is directly input through the switching circuit 65 of the Doppler spectrum generating unit 7 to the A/D converter 63, converted into a digital signal, and then subjected to frequency analysis at the FFT analyzer 64. It is to be noted that since the continuous wave Doppler method does not have distance resolution, a plurality of Doppler signal components obtained by moving reflectors of different depths in a predetermined ultrasound wave transmitting/receiving direction are superimposed to be received.

FIGS. 4A and 4B schematically show an FFT analyzing method of the FFT analyzer 64: FIG. 4A showing a Doppler signal Ao input to the FFT analyzer 64, and FIG. 4B a frequency spectrum Bx (x=1, 2, . . . ) obtained by analyzing a predetermined period of the Doppler signal Ao. Then, FFT analysis is carried out for, e.g., m pieces of Doppler signal components of g1 to qm among discrete Doppler signals (FIG. 4A) output from the A/D converter 63 of the Doppler spectrum generating unit 7, and a first frequency spectrum B1 for spectrum components p1 to pm is measured. Subsequently, m pieces of Doppler signal components of q1+j to qm+j after a time ΔT are subjected to FFT analysis to measure a new frequency spectrum B2. It is to be noted that FIG. 4A shows a case of J=3.

Thereafter, similarly, FFT analysis is sequentially carried out for m pieces of Doppler signal components of q1+2j to qm+2j after a time 2ΔT, q1+2j to qm+3j after a time 3 ΔT . . . to measure frequency spectra B3, B4, . . . for the spectrum components p1 to pm (FIG. 4B).

Next, returning to FIG. 1, the data processing/storing unit 70 comprises a data storing unit 8 and a data processing unit 9. The data storing unit 8 sequentially saves B-mode data, color Doppler data and Doppler spectrum data generated by scanning direction units at the data generating unit 50, and generates two-dimensional B-mode image data, color Doppler image data and spectrum data. Further, cine-data generated by the data processing unit 9 using the spectrum data is saved.

On the other hand, the data processing unit 9 performs image processing and scanning conversion (scan conversion)

for the B-mode image data and the color Doppler image data, generation of tracing data for a maximum frequency component of the spectrum data, and generation of cine-data by synthesizing high-power mode spectrum data generated under control of the acoustic power controller 80, or the like.

Figures 5A, 5B:
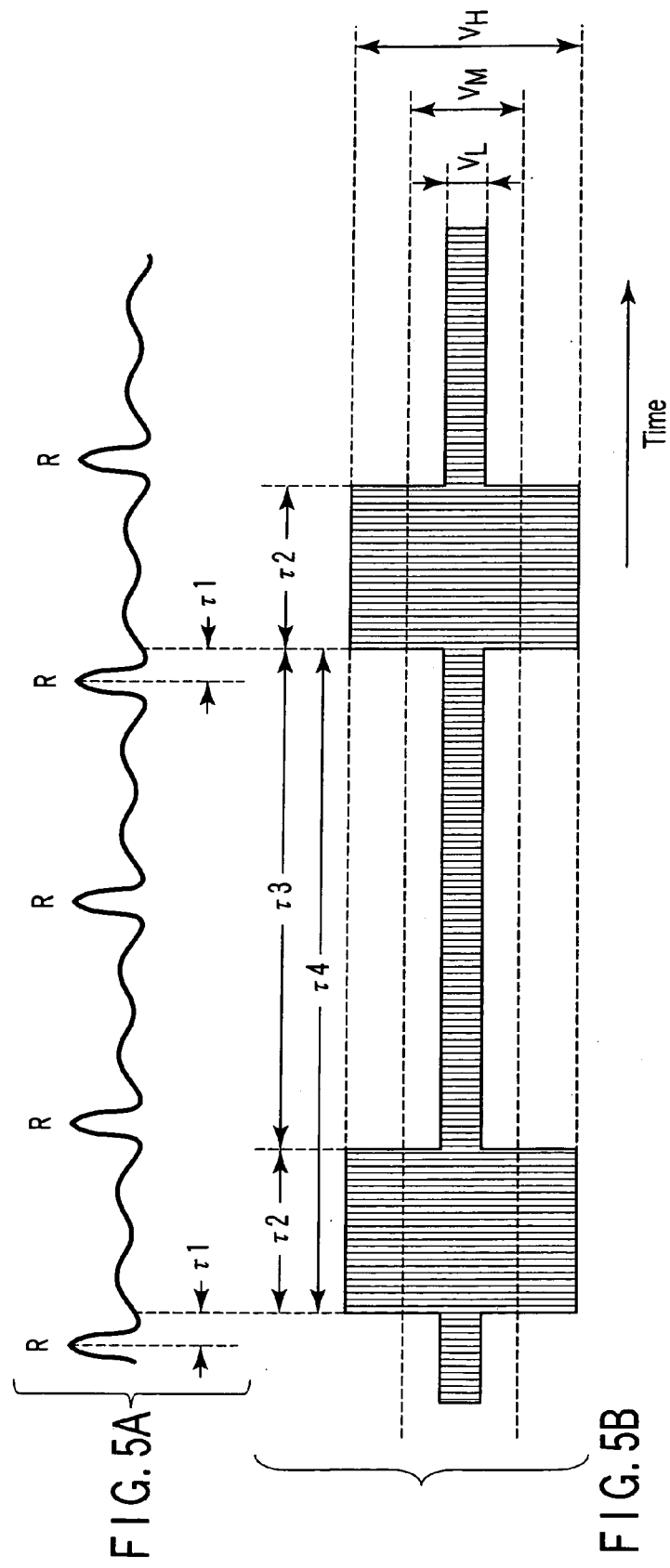
FIGS. 5A and 5B are graphs showing a piezoelectric transducer driving method in a continuous wave Doppler method of the first embodiment.

Next, the acoustic power controller 80 comprises the processing circuit and the storing unit (not shown), and performs various settings such as a high-power mode and a low-power mode in the pulse Doppler method or the continuous wave Doppler method. FIGS. 5A and 5B show a piezoelectric transducer driving method of the continuous wave Doppler method. Hereinafter, a case of controlling transmitted acoustic power based on a piezoelectric transducer driving voltage and a driving period will be described. However, the invention is not limited to this. For example, a wave number of a driving pulse may be controlled in the case of the pulse Doppler method.

That is, FIG. 5A shows an ECG waveform obtained from the subject, FIG. 5B a voltage waveform applied from the driving circuit 43 of the transmitter 2 to the piezoelectric transducer of the probe 20 in synchronization with this ECG waveform. For example, driving of a high-power mode of a driving voltage (amplitude voltage) $V_H$ is started after a predetermined delay time τ1 preset from an R wave of the ECG waveform, and this high-power mode is changed to a low-power mode of a diving voltage $V_L$ after continuance of a period τ2. A center frequency of the driving voltage of the high-power mode is roughly equal to that of the driving voltage of the low-power mode. Further, the low-power mode is changed again to the high-power mode of the driving voltage $V_H$ after a period τ3. It is to be noted that a driving voltage $V_M$ shown in FIG. 5B indicates a driving voltage in a conventional continuous wave Doppler method, and a relation of $V_L < V_M < V_H$ is established.

Here, assuming that an upper limit of transmitted acoustic power permitted per unit time is W0, a relation between the driving voltages $V_L$, $V_M$ and $V_H$ and the driving periods τ2 and τ3 is represented by the following equation (1), in which W indicates transmitted acoustic power per unit time and K indicates a proportionality constant according to the embodiment.

$$W = K(V_H^2 \tau 2 + V_L^2 \tau 3)/(\tau 2 + \tau 3) < W0 \approx K V_H^2 \quad (1)$$

That is, according to the equation (1), the transmitted acoustic power per unit time is decided by the driving period τ2 and the driving voltage $V_H$ of the high-power mode and the driving period τ3 and the driving voltage $V_L$ of the low-power mode. Three among the four parameters are set by the operator, whereby an optimal value for the permitted acoustic output W0 of the remaining parameter can be calculated. Specifically, by setting the driving voltage $V_H$ and the driving period τ2 of the high-power mode and the driving voltage $V_L$ of the low-power mode, preferably, the period τ3 of the low-power mode, i.e., a repeating cycle τ4 (τ4=τ2+3) of the high-power mode, is calculated. However, there is no particular limitation on parameters to be calculated.

A processing program based on the equation (1) is pre-stored in the storing circuit of the acoustic power controller 80. For example, the processing circuit calculates an optimal value of the remaining parameter by using the processing program and the three parameter values fed through the system controller 19.

Next, the display unit 15 comprises a display data generating unit, a converting circuit and a monitor (not shown). The B-mode image data, the color Doppler image data and the spectrum data generated at the data processing/storing unit 70, and the cine-data of the spectrum data are synthesized by the display data generating circuit to generate display data. This display data is subjected to D/A conversion and television bit format conversion by the converting circuit, and displayed on the monitor.

On the other hand, the input unit 17 comprises a display panel on an operation panel and input devices such as a keyboard, a trackball, a mouse, selection buttons, and input buttons, inputs patient information, sets a data collection mode, display conditions and the like, and inputs various command signals, and the like. Especially, in the pulse Doppler method or the continuous wave Doppler method, the driving start timing and the driving period τ2 of the high-power mode, the driving voltages $V_H$ and $V_L$ of the high-power and low-power modes, a transmitting/receiving direction (θD) for data collection, a range gate position (Lg) and the like are set. The driving start timing in the high-power mode is usually set based on the ECG signal of the subject as shown in FIGS. 5A and 5B. However, the operator may directly set the timing by using the input device (input button) of the input unit 17.

FIGS. 17 and 18 show examples of Doppler condition setting screens generated by the system controller 19: FIG. 17 showing the setting screen when a high-power mode is set in a partial period of a heartbeat cycle and a low-power mode is set in a remaining period, and FIG. 18 the setting screen when a high-power mode is set in one or a predetermined number of continuous heartbeat periods of the subject, and a low-power mode is set in a predetermined number of continuous heartbeat periods of the subject. On the screens, an electrocardiographic waveform 215 of the subject is displayed together with a B-mode image 200 on which a range gate 203 is superimposed. Additionally, on the screens, a button expressed as "Vmax", a button expressed as "All Wave", and increase/decrease buttons 209, 211 are displayed together with a line mark 213 indicating a continuance period of the high-power mode. A period other than that indicated by the line mark 213 is a continuance period of the low-power mode.

The button "Vmax" corresponds to the purpose of inspecting a highest flow velocity by a high S/N ratio by setting the high-power mode in the partial period of the heartbeat cycle. When the button "Vmax" is clicked, as illustrated in FIG. 17, the system controller 19 arranges the line mark 213 of a length equivalent to a time width t2 preferable for highest flow velocity inspection in a position delayed by a delay time (initial value) t1 from an R wave suited to the highest flow velocity inspection. The delay time t1 and the continuance period t2 are displayed together with the line mark 213 in numerical sections 217, 219. When the button "Vmax" is clicked, the increase/decrease buttons 209, 211 are set in unselective states. By operating the input unit 17, the operator moves the line mark 213 to a desired position to adjust it to a desired length. Additionally, the operator can directly input numerical values of the delay time t1 and the continuance period t2 in the numerical value sections 217, 219 by operating the input unit 17. Accordingly, periods and continuance periods of the high-power and low-power modes are set.

The button "All Wave" corresponds to the purpose of setting the high-power mode in one or a predetermined number of continuous heartbeat periods of the subject, and the low-power mode in a predetermined number of continuous heartbeat periods. When the button "All Wave" is clicked, the increase/decrease buttons 209, 211 set in selective states to be operated. When the button "All Wave" is clicked, as illustrated in FIG. 18, the system controller 19 arranges a plurality of line marks 213 having lengths equivalent to one initially set heartbeat period at intervals having lengths equivalent to three initially set heartbeat periods. A length of the line mark 213 corresponds to the continuance period of the high-power mode. An interval between the pair of line marks 213 corresponds to the continuance period of the low-power mode. When the continuance period of the high-power mode is increased/decreased, the operator operates the increase/decrease button 209. The continuance period of the high-power mode is increased/decreased by a heartbeat period unit. The length of the line mark 213 is extended/shortened in accordance with the increase/decrease of the continuance period of the high-power mode. When the continuance period of the low-power mode is increased/decreased, the operator operates the increase/decrease button 211. The continuance period of the low-power mode is also increased/decreased by a heartbeat period unit. The interval between the pair of line marks 212 is expanded/reduced in accordance with the increase/decrease of the continuance period of the low-power mode.

The system controller 19 comprises a CPU and a storing circuit (not shown). Various pieces of information input or set beforehand from the input unit by the operator are saved in the storing circuit. The CPU controls the transmitting/receiving unit 40, the data generating unit 50, the data processing/storing unit 70, the acoustic power controller 80 and the display unit 15, or the entire system overall based on the pieces of information.

Next, the ECG unit 18 is provided for collecting electrocardiographic waves of the subject. Based on any one of P, Q, R, S and T waves of the electrocardiographic waves obtained by the ECG unit 18, the driving start timing of the high-power mode is set in the pulse Doppler method or the continuous wave Doppler method.

Next, the piezoelectric transducer driving method in the pulse Doppler method or the continuous wave Doppler method of the embodiment, and the spectrum data obtained by the driving will be described by referring to FIGS. 6A and 6B.

Figures 6A, 6B:
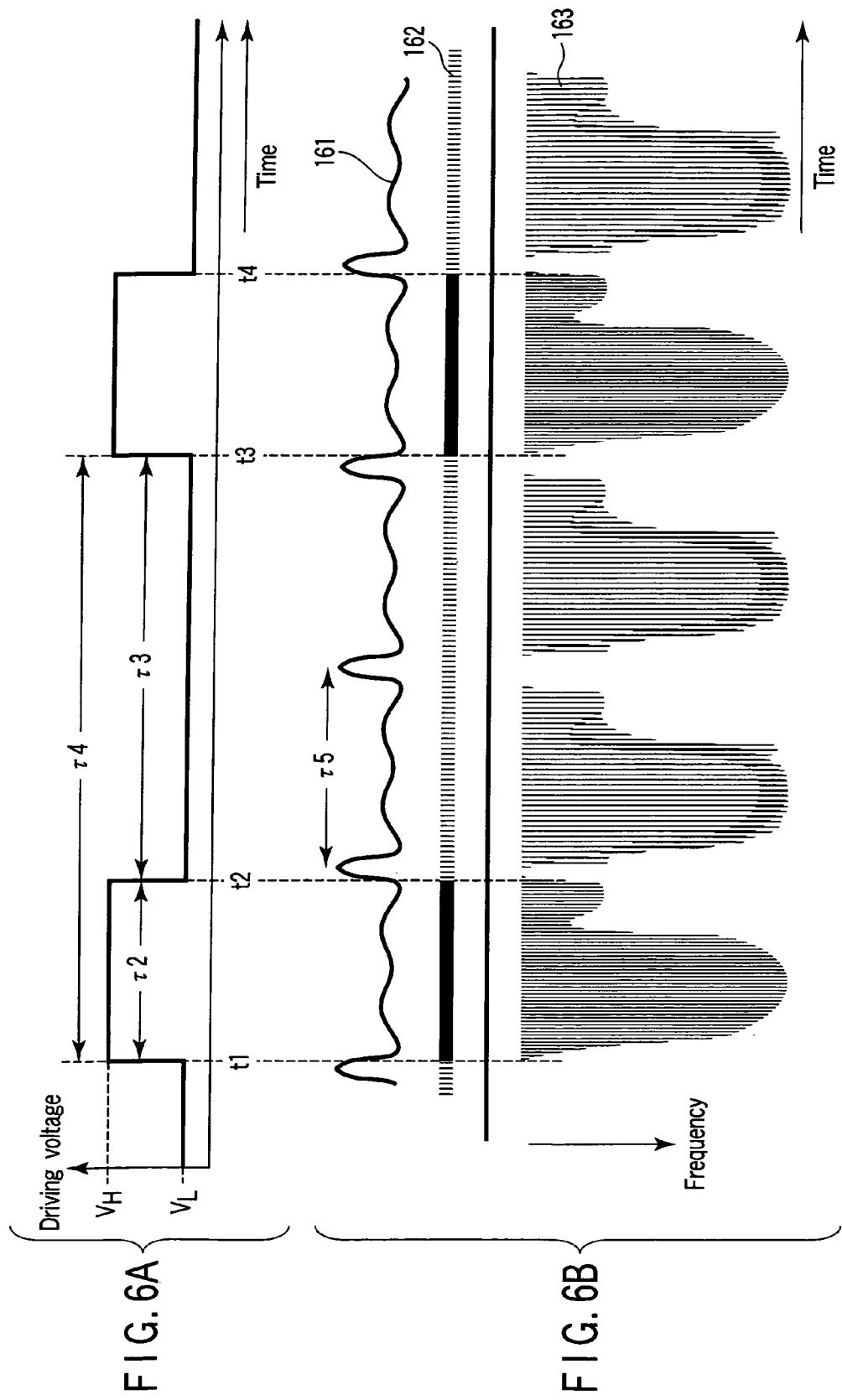
FIGS. 6A and 6B are graphs showing the piezoelectric transducer driving method of the first embodiment and spectrum data obtained by its driving.

FIGS. 6A and 6B show a case of setting driving start timings t1, t3 . . . , a driving period τ2 and a driving cycle τ4 of the high-power mode based on the ECG wave fed from the ECG unit 18: FIG. 6A showing the driving voltages $V_H$, $V_L$ and the driving periods τ2, τ3 of the high-power and low-power modes, FIG. 6B an ECG wave 161 obtained from the subject at a cycle τ5, a high-power indicator 162 indicating the driving period of the high-power mode, and spectrum data 163 generated by the driving voltage of FIG. 6A. Then, the ECG wave 161 and the high-power indicator 162 are displayed together with the spectrum data 163 on the monitor of the display unit 15.

It is to be noted that the high-power mode indicator 162 is first displayed based on the initially set driving start timing and driving period of the high-power mode, and the operator can set a new driving period of the high-power mode by updating the position and the length of the indicator by using the input device of the input unit 17.

(Procedure of Generating Spectrum Data)

Figure 7:
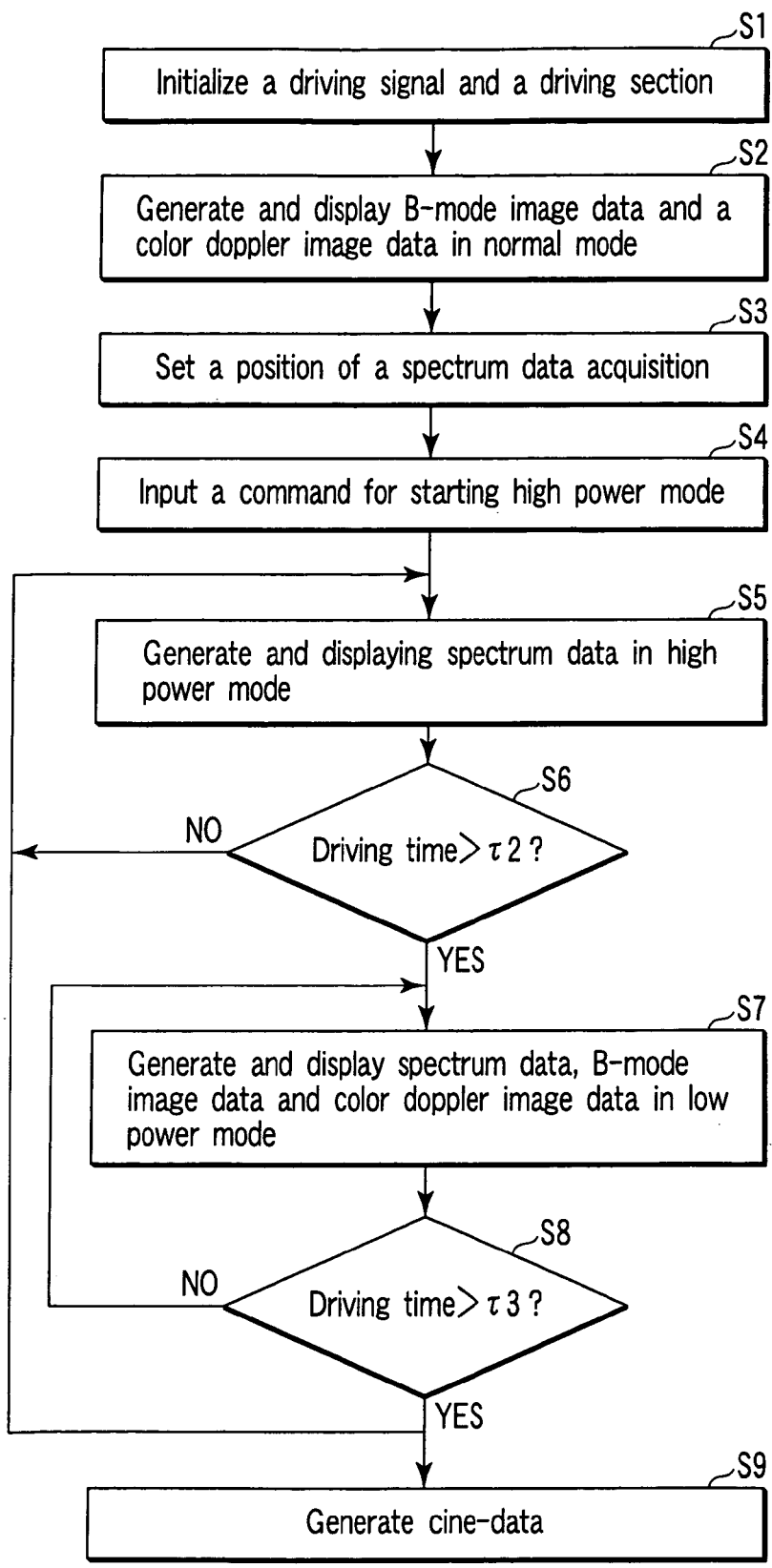
FIG. 7 is a flowchart showing a procedure of generating the spectrum data of the first embodiment.
Figure 9:
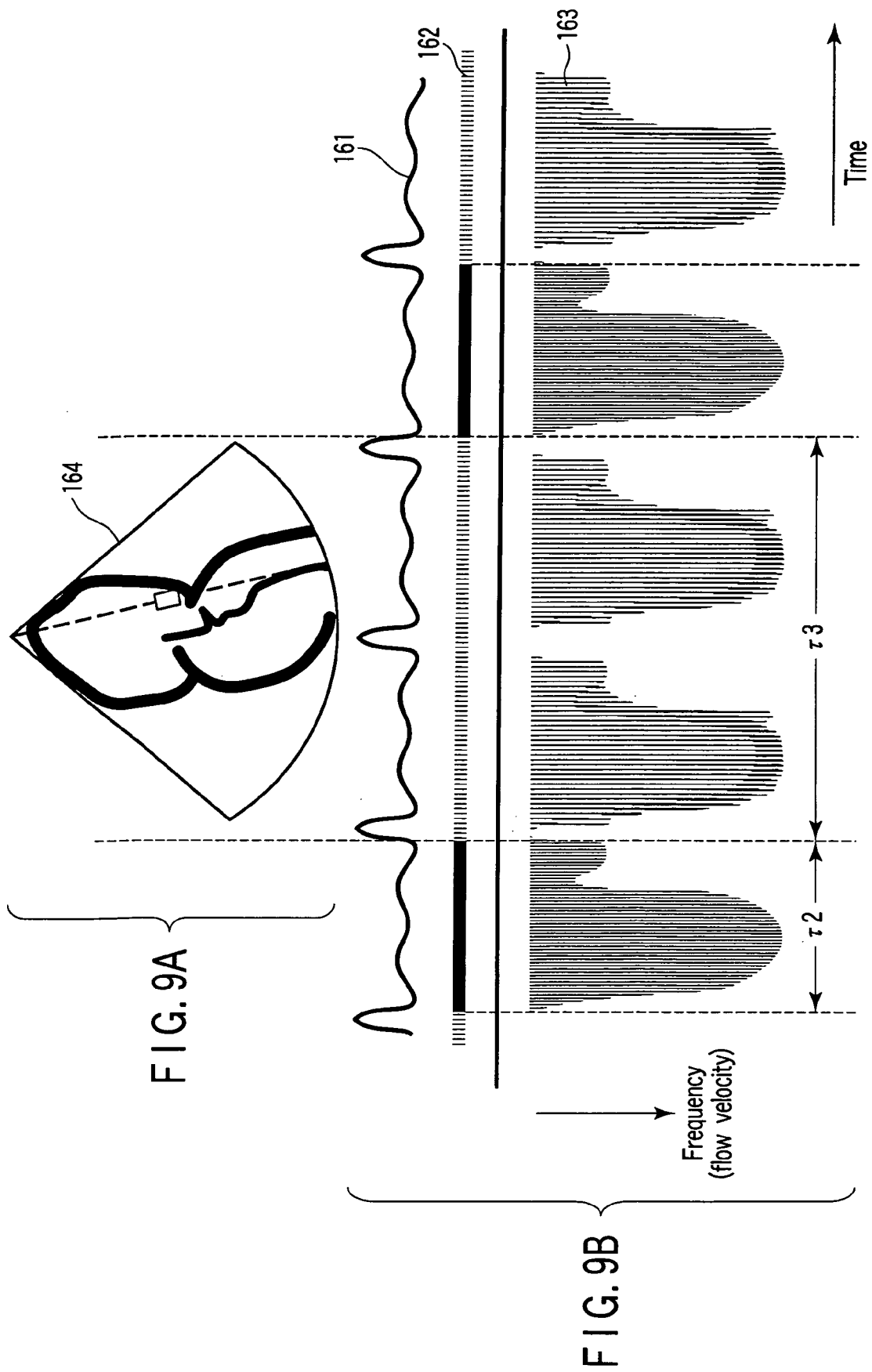
FIGS. 9A and 9B are graphs showing spectrum data, B-mode image data and color Doppler image data obtained in the low-power mode of the first embodiment.

Next, a procedure of generating spectrum data according to the embodiment will be described with reference to FIGS. 1 to 12C. FIG. 7 is a flowchart showing the generation procedure of the embodiment. The pulse Doppler method will be mainly described in the embodiment. However, spectrum data can be generated by a roughly similar procedure in the continuous wave Doppler method.

Before collecting ultrasound data, the operator first inputs patient information by the input unit 17, and selects a selection mode of B-mode image data, color Doppler image data and spectrum data. Subsequently, as shown in FIG. 8, the operator sets driving voltages $V_H$, $V_L$ of the high-power and low-power modes in the pulse Doppler method, driving voltages $V_{BH}$, $V_{BL}$ of a normal mode and a low-power mode in the B-mode method, and a driving start timing τ1 and a driving period τ2 of the high-power mode. Then, these pieces of information are saved in the storing unit (not shown) of the system controller 19 (step S1 of FIG. 7).

After the end of the initial setting, the operator fixes the tip (ultrasound wave transmitting/receiving surface) of the ultrasound probe 20 to a predetermined position of the subject surface, whereby ultrasound wave transmission/reception is carried out to obtain B-mode data of a first scanning direction (θ1 direction) in the normal mode. In other words, the rate pulse generator 41 of FIG. 2 generates a rate pulse for deciding a repeating cycle Tr of an ultrasound pulse by frequency-dividing a reference signal fed from the reference signal generating unit 1, and feeds the rate pulse to the transmitting delay circuit 42.

Subsequently, the transmitting delay circuit 42 gives a converging delay time for converging ultrasound waves to a predetermined depth and a deflecting delay time for transmitting ultrasound waves in the first scanning direction (θ1) to the rate pulse, and feeds this rate pulse to the driving circuit 43. Then, the driving circuit 43 feeds a driving signal of a driving voltage $V_{BH}$ generated by driving the rate pulse through the cable to N pieces of piezoelectric transducers in the ultrasound probe 20, and emits an ultrasound pulse in the first scanning direction.

A part of the ultrasound pulse emitted to the subject is reflected on a boundary or a tissue between organs of different acoustic impedances. If the ultrasound wave is reflected on a moving reflector such as a heart wall or a blood cell, its frequency receives Doppler deviation.

The ultrasound reflected wave (received ultrasound wave) reflected on the tissue or the blood cell of the subject is received by the piezoelectric transducer of the ultrasound probe 2, and converted into an electric signal (received signal). This received signal is amplified by the N-channel independent amplifier 44 in the receiver 3, and sent to the N-channel receiving delay circuit 45.

The receiving delay circuit 45 gives a converging delay time for converging ultrasound waves from a predetermined depth and a deflecting delay time for receiving ultrasound waves in the first scanning direction by providing strong receiving directivity to the received signal, and then sends the received signal to the adder 46. Then, the adder 46 adds and synthesizes N-channel received signals output from the receiving delay circuit 45, converges them into one received signal, and then feeds it to the B-mode data generating unit 4.

Next, an output signal of the adder 46 is subjected to logarithmic transformation, envelope detection and A/D conversion at the B-mode data generating unit 4, and then saved in the data storing unit 8 of the data processing/storing unit 70 of FIG. 1.

On the other hand, in the generation of the color Doppler image data in the normal mode, to obtain Doppler deviation of a received signal, by a procedure similar to the above, ultrasound wave transmission/reception is continuously carried out by a plurality of times in the first scanning direction, and frequency analysis is performed for the received signal thereby obtained.

That is, the system controller 19 sets a driving voltage $V_{CH}$ of the driving circuit 43, and performs first color Doppler ultrasound wave transmission/reception in the first scanning direction. Then, the obtained received signal is fed to the Doppler signal detecting unit 5, and subjected to orthogonal phase detection by the mixers 55-1 55-2 and LPF's 56-1 and 56-2 to generate a two-channel complex signal. Subsequently, real and imaginary components of the complex signal are converted into digital signals by the A/D converter 57 of the color Doppler data generating unit 6, and then saved in the Doppler signal storing unit 58. A similar process is carried out for received signals obtained by 2nd to Lth ultrasound wave transmission/reception in the first scanning direction to collect complex signals, and the complex signals are saved in the Doppler signal storing unit 58.

After the end of storing the complex signal obtained by the Lth ultrasound wave transmission/reception in the first scanning direction in the Doppler signal storing unit 58, the system controller 19 sequentially reads complex signal components corresponding to predetermined positions (depths) from the complex signals saved in the Doppler signal storing unit 58, and feeds them to the MTI filter 59. Then, the MTI filter 59 performs filter processing for the fed complex signals, removes tissue Doppler components (cluttering components) generated by, e.g., motion of a tissue such as a heart muscle, and extracts only blood flow Doppler components caused by a blood flow.

The auto correlation processing unit 60 that has received the complex signals performs auto correlation processing by using the complex signals, and calculates an average blood flow velocity value or a distribution value or a power value based on a result of the auto correlation processing. This processing is also carried out for other positions (depths) in the first scanning direction, and a calculated average blood flow velocity value, a distribution value or a power value is saved in the data storing unit 8 of the data processing/storing unit 70 of FIG. 1.

Then, the system controller 19 performs similar ultrasound wave transmission/reception in second to Mth scanning directions (θ2 to θM). Then, B-mode data and color Doppler data thus obtained are saved in the data storing unit 8.

By the aforementioned procedure, the B-mode data and the color Doppler data obtained by the scanning direction units are sequentially saved in the data storing unit 8 to generate B-mode image data and color Doppler image data. These data are subjected to image processing and scanning conversion at the data processing unit 9. Then, the display data generating circuit of the display unit 15 synthesizes the image data after the scanning conversion to generate display data. This display data is fed to the converting circuit, subjected to D/A conversion or TV format conversion, and displayed on the monitor (step S3 of FIG. 7).

Next, the operator moves a marker (direction marker) indicating a scanning direction (θD) for collecting spectrum data and a marker (range gate marker) indicating a distance (Lg) with respect to the displayed image data by using the input device of the input unit 17, and sets the markers in optimum positions (step S3 of FIG. 7). Subsequently, after the position for collecting the spectrum data has been decided, a driving start command of the high-power mode is input by the input unit 17 (step S4 of FIG. 7).

The system controller 19 that has received the command signal temporarily stops the generation of the B-mode data and the color Doppler data, and then the acoustic power controller 80 controls the driving circuit 43 of the transmitter 2 so that a piezoelectric transducer driving voltage can become $V_H$. Subsequently, ultrasound wave transmission/reception is carried out in the scanning direction θD to collect spectrum data, and an output signal (received signal) of the adder 46 is fed to the Doppler signal detecting unit 5.

As shown in FIGS. 3A to 3G, the Doppler signal detecting unit 5 feeds a complex signal obtained by subjecting the received signal to orthogonal phase detection to the SH 62 of the Doppler spectrum generating unit 7. On the other hand, a sampling pulse corresponding to the range gate position Lg set by the operator is fed to the SH 61 by the system controller 19, and the complex signal is sample-held based on the sampling pulse. Then, outputs of the SH 61 obtained by ultrasound wave transmission/reception carried out by a plurality of times at a cycle Tr in the scanning direction θD are smoothed through the HPF 62, converted into digital signals by the A/D converter 63, and saved in the storing unit (not shown) of the FFT analyzer 64.

As shown in FIGS. 4A and 4B, the processing circuit (not shown) of the FFT analyzer 64 sets a plurality of periods shifted by predetermined times (ΔT) for continuously collected Doppler signals, and performs FFT analysis for the Doppler signals of the periods to generate Doppler spectra.

That is, as shown in FIG. 4A, the processing circuit of the FFT analyzer 64 reads, e.g., m pieces of signal components of g1 to qm to carry out FFT analysis for discrete Doppler signals obtained at a rate pulse cycle Tr, and calculates a Doppler spectrum B1 constituted of spectrum components p1 to pm. The calculated Doppler spectrum B1 is fed to the data storing unit 8 of the data processing/storing unit 70.

Thereafter, similarly, for m pieces of Doppler signals after a time ΔT, after a time 2ΔT, after a time 3ΔT . . . , the FFT analyzer 64 of the Doppler spectrum generating unit 7 calculates Doppler spectra B2, B3, B4 . . . Then, the plurality of calculated Doppler spectra are saved in sonogram forms in the data storing unit 8 to generate spectrum data of the high-power mode. The spectrum data is displayed by the display unit 15 (step S5 of FIG. 7).

When the driving period of the high-power mode reaches a preset period τ2 (step S6 of FIG. 7), the system controller 19 restores the generation of the B-mode image data and the color Doppler image data. Subsequently, the acoustic power controller 80 sets a B-mode driving voltage $V_{BL}$ ($V_{BL}<V_{BH}$), a color Doppler driving voltage $V_{CL}$ ($V_{CL}<V_{CH}$) and a pulse Doppler driving voltage $V_L$ ($V_L<V_H$) of the low-power mode.

Then, B-mode data, color Doppler data and spectrum data are generated by a method similar to the above. Based on these data, the B-mode image data, the color image data and the spectrum data generated by the data processing/storing unit 70 are displayed on the monitor of the display unit 15 (step S7 of FIG. 7).

On the other hand, the acoustic power controller 80 pre-calculates a driving period τ3 of the low-power mode by substituting the driving voltage $V_H$ and the driving period τ2 of the high-power mode time and the driving voltage $V_L$ of the low-power mode time for the equation (1), and returns the mode to the high-power mode again after the driving period τ3 of the low-power mode is reached (step S8 of FIG. 7). It is to be noted that the equation (1) can be directly applied when the B-mode driving voltage $V_{BL}$ and the color Doppler driving voltage $V_C$ of the low-power mode are roughly equal to the pulse Doppler driving voltage $V_L$. If they are different, however, the driving period τ3 must be calculated by correcting the driving voltage of the low-power mode time.

The generation and the displaying of the spectrum data of the high-power and low-power modes are alternately carried out by the aforementioned procedure. Further, in addition to the spectrum data of the low-power mode, B-mode image data and color Doppler image data 164 of the low-power mode similar to those shown in FIGS. 9A and 9B are generated and displayed (steps S5 to S8 of FIG. 7).

Figure 10:
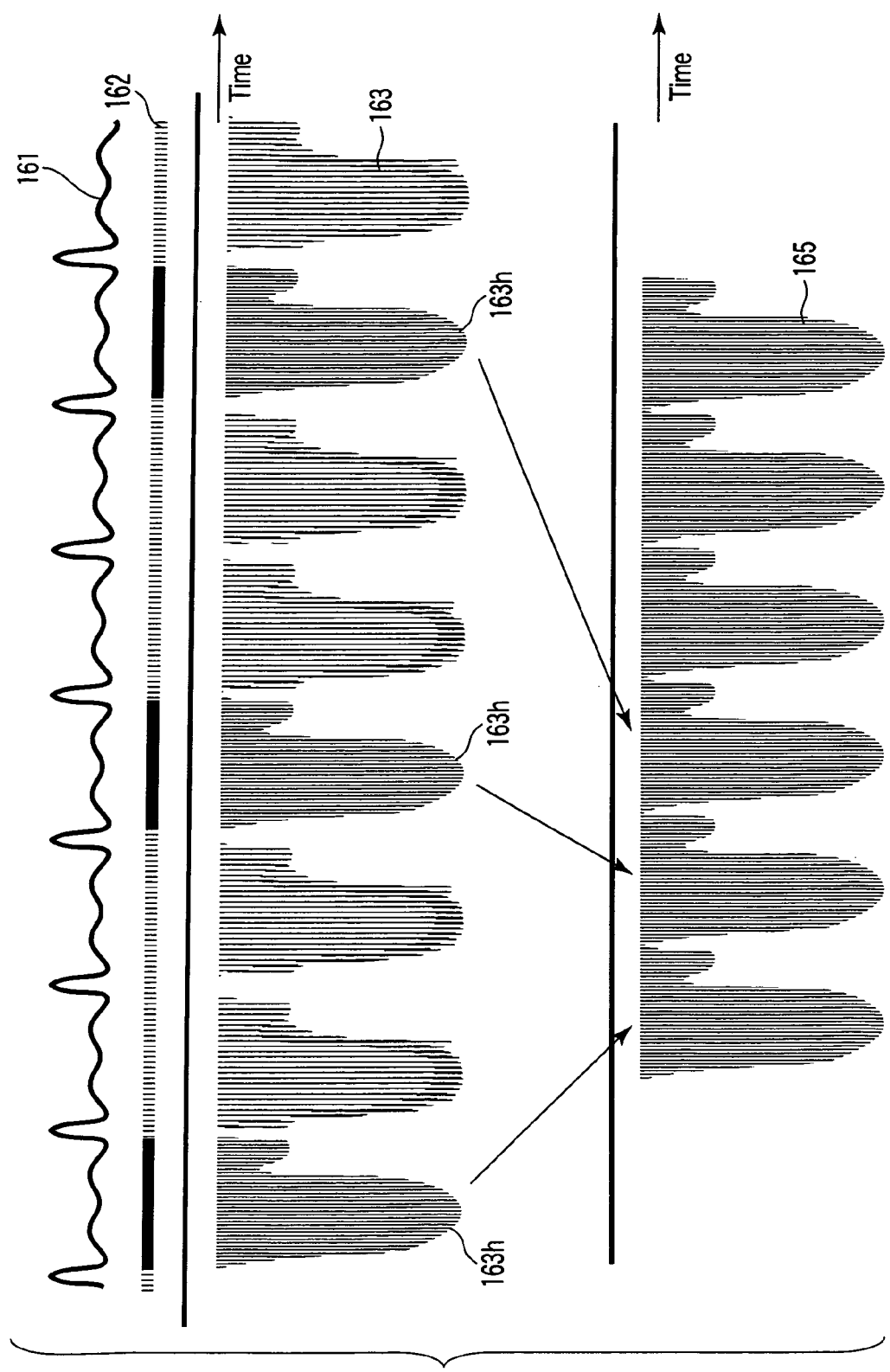
FIG. 10 is a graph showing cine-data generated by synthesizing the spectrum data obtained in the high-power mode of the first embodiment.

On the other hand, as shown in FIG. 10, the data processing unit 9 of the data processing/storing unit 70 extracts the spectrum image data 163h of the high-power mode from the spectrum data 163 obtained by alternately repeating the high-power and low-power modes to generate cine-data 165 (step S9 of FIG. 7), saves the cine-data in the cine-data storing area of the data storing unit 8, and displays it on the monitor of the display unit 15 when necessary.

Figure 11:
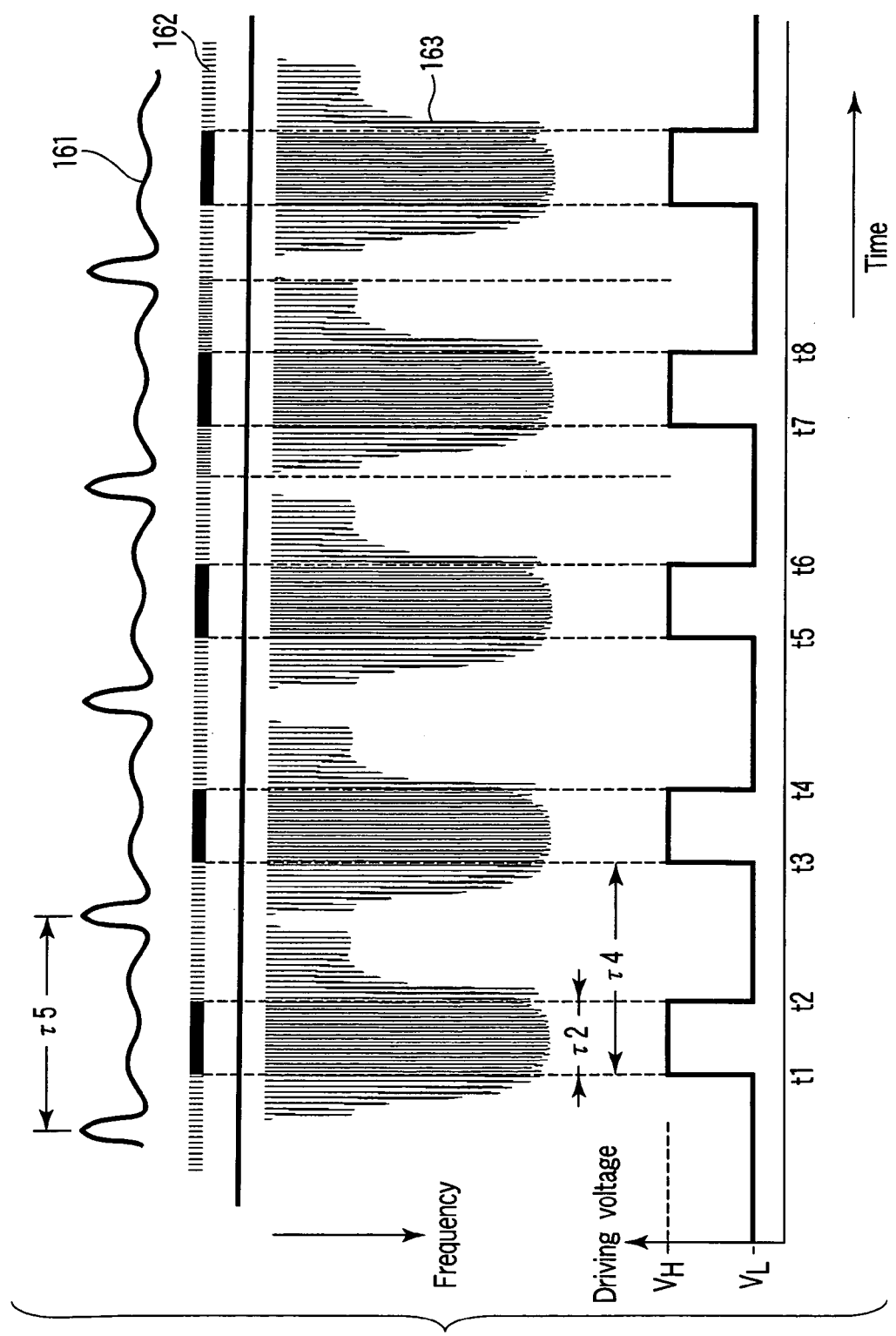
FIG. 11 is a graph showing the piezoelectric transducer driving method of the first embodiment and another specific example of spectrum data obtained by its driving.
Figure 12:
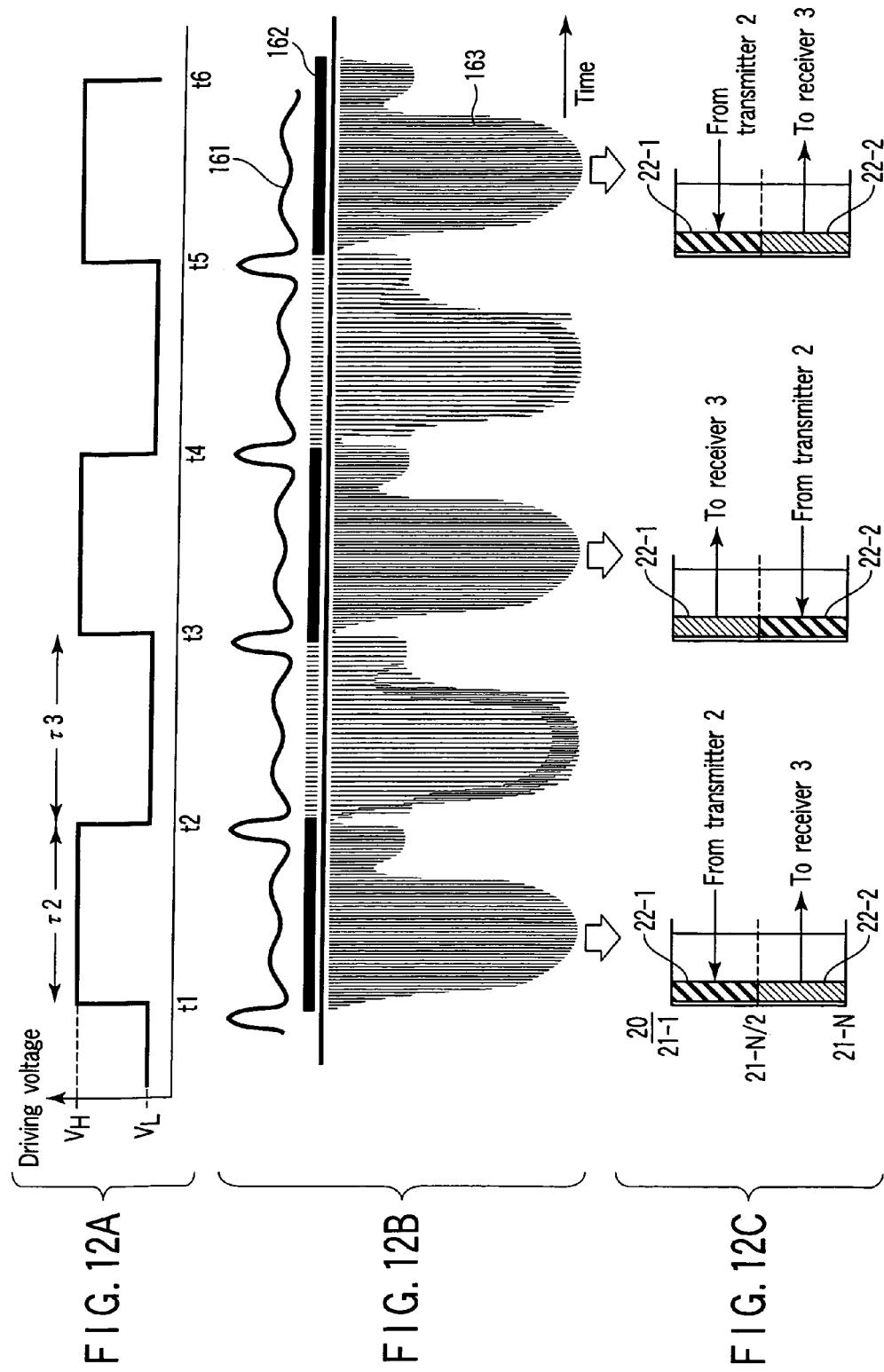
FIGS. 12A to 12C are graphs showing a piezoelectric transducer switching driving method according to a modified example of the first embodiment.

The case in which the driving cycle τ4 of the high-power mode is larger than a heartbeat cycle τ5 has been described with reference to FIGS. 6A and 6B. However, the invention can be applied to a case in which τ4<τ5 can be established as shown in FIG. 11. That is, as shown in FIG. 11, when the driving start timings t1, t3, t5, t7 . . . , the driving period τ2 and the driving cycle τ4 of the high-power mode are set based on the ECG waveform 161, by setting the driving period τ2 of the high-power mode only in a portion of one heartbeat in which, e.g., a maximum frequency component (maximum flow velocity value) is obtained, it is possible to observe clinically important information with good sensitivity.

The embodiment has been described by taking the example of generating and displaying the spectrum data in the pulse Doppler method. However, spectrum data can be obtained by a similar procedure in the continuous wave Doppler method. That is, the driving circuit 43 of the transmitter 2 generate a continuous wave driving signal based on the continuous wave of the reference signal generating unit 1 fed through the transmitting delay circuit 42, and feeds this signal to the first transducer group of the ultrasound probe 20. On the other hand, the received signal obtained by the transducer group of the second transducer group of the ultrasound probe 20 is sent through the receiver 3, the Doppler signal detecting unit 5, and the A/D converter 63 and the FFT analyzer 64 of the Doppler spectrum generating unit 7 to the data processing/storing unit 70, and spectrum data is generated.

MODIFIED EXAMPLE

Next, a modified example of the embodiment will be described with reference to FIGS. 12A to 12C. A feature of the modified example is that when spectrum data of a high-power mode is generated by a continuous wave Doppler method, N pieces of piezoelectric transducers of an ultrasound probe 20 are classified into a first transducer group and a second transducer group adjacent to the first, and the transducer group for transmission and the transducer group for reception are alternately switched to be used.

FIGS. 12A to 12C show a case of generating spectrum data by repeating high-power and low-power modes at one heartbeat cycle of an ECG waveform: as in the case of FIGS. 6A and 6B, FIG. 12A showing driving voltages $V_H$, $V_L$ and driving periods τ2, τ3 of the high-power and low-power modes, FIG. 12B spectrum data 163 obtained together with an ECG waveform 161 and a high-power indicator 162, and FIG. 12C a transducer group 22 of the ultrasound probe 20 used for transmission/reception of the high-power mode period τ2.

For example, N pieces of piezoelectric transducers 21-1 to 21-N constituting the ultrasound probe 20 are classified into a first transducer group 22-1 constituted of the piezoelectric transducers 21-1 to 21-N/2, and a second transducer group 22-2 constituted of the piezoelectric transducers 21-(N/2+1) to 21-N. In a first high-power mode period of a time t1 to a time t2, ultrasound waves are emitted by using the first transducer group 22-1, and received ultrasound waves are detected by using the second transducer group 22-2. On the other hand, in a second high-power mode period of a time t3 to t4, the first transducer group 22-1 is used for reception, and the second transducer group 22-2 is used for transmission. Further, in a third high-power mode period of a time t5 to t6, as in the case of the first high-power mode period, the first transducer group 22-1 is used for transmission, and the second transducer group 22-2 is used for reception.

Accordingly, by performing ultrasound wave transmission/reception in the high-power mode while alternately switching the transmission transducer group and the reception transducer group, the amount of generated heat in the first or second transducer group 22-1 or 22-2 is reduced by about ½ as compared with the conventional case.

As described above, according to the first embodiment, the ultrasound wave transmission/reception is carried out by classifying the spectrum data generation period of the ultrasound Doppler spectrum method into the high-power mode period having transmitted acoustic power larger than that of the conventional method and the low-power mode period of transmitted acoustic power smaller than that of the conventional method. Thus, it is possible to generate spectrum data of high sensitivity without increasing the transmitted acoustic power per unit time.

Especially, the transmitted acoustic power and the driving periods of the high-power and low-power modes are set based on the heat generation regulations or the acoustic power regulations. Thus, the regulations can be complied with by limiting the overall output low, and a clinically required Doppler spectrum or a portion of the spectrum data to be observed can be obtained. Accordingly, generation of tracing data for, e.g., a maximum frequency component of the spectrum data is facilitated, a load on the operator is reduced, and diagnosing efficiency is increased.

It is not proper for performing diagnosis by using low-sensitivity spectrum data generated in the low-power mode period. However, by observing this data, it is possible to confirm a normal operation of the apparatus.

Effects similar to the above can be provided for the B-mode image data and the color Doppler image data displayed in the low-power mode period. That is, the collecting position of the spectrum data can be always monitored by the direction marker and the range gate marker shown on the image data. If the position is not proper, it can be changed to an optimal position by using the input device of the input unit.

Furthermore, according to the modified example of the first embodiment, by switching and using the transmission transducer group and the reception transducer group for each repeated high-power mode in the continuous wave Doppler method, it is possible to reduce the amount of generated heat in the ultrasound probe. Thus, the driving voltage of the high-power mode can be increased, and the spectrum data can be generated with higher sensitivity.

Second Embodiment

Next, a second embodiment of the present invention will be described with reference to FIGS. 13 to 15. A feature of the embodiment is that spectrum data is generated in a high-power mode based on a driving start command signal which an operator inputs by an input unit.

A configuration of an ultrasound diagnostic apparatus of the second embodiment is similar to the ultrasound diagnostic apparatus 100 of the first embodiment shown in FIGS. 1 and 2, and thus description thereof will be omitted. A procedure of generating spectrum data according to the embodiment will be described by referring to a flowchart of FIG. 13. However, steps of the flowchart similar to those of the flowchart of FIG. 7 of the first embodiment will be omitted. The embodiment will be described by way of mainly a pulse Doppler method. However, spectrum data can be generated by a roughly similar method in a continuous wave Doppler method.

Figure 13:
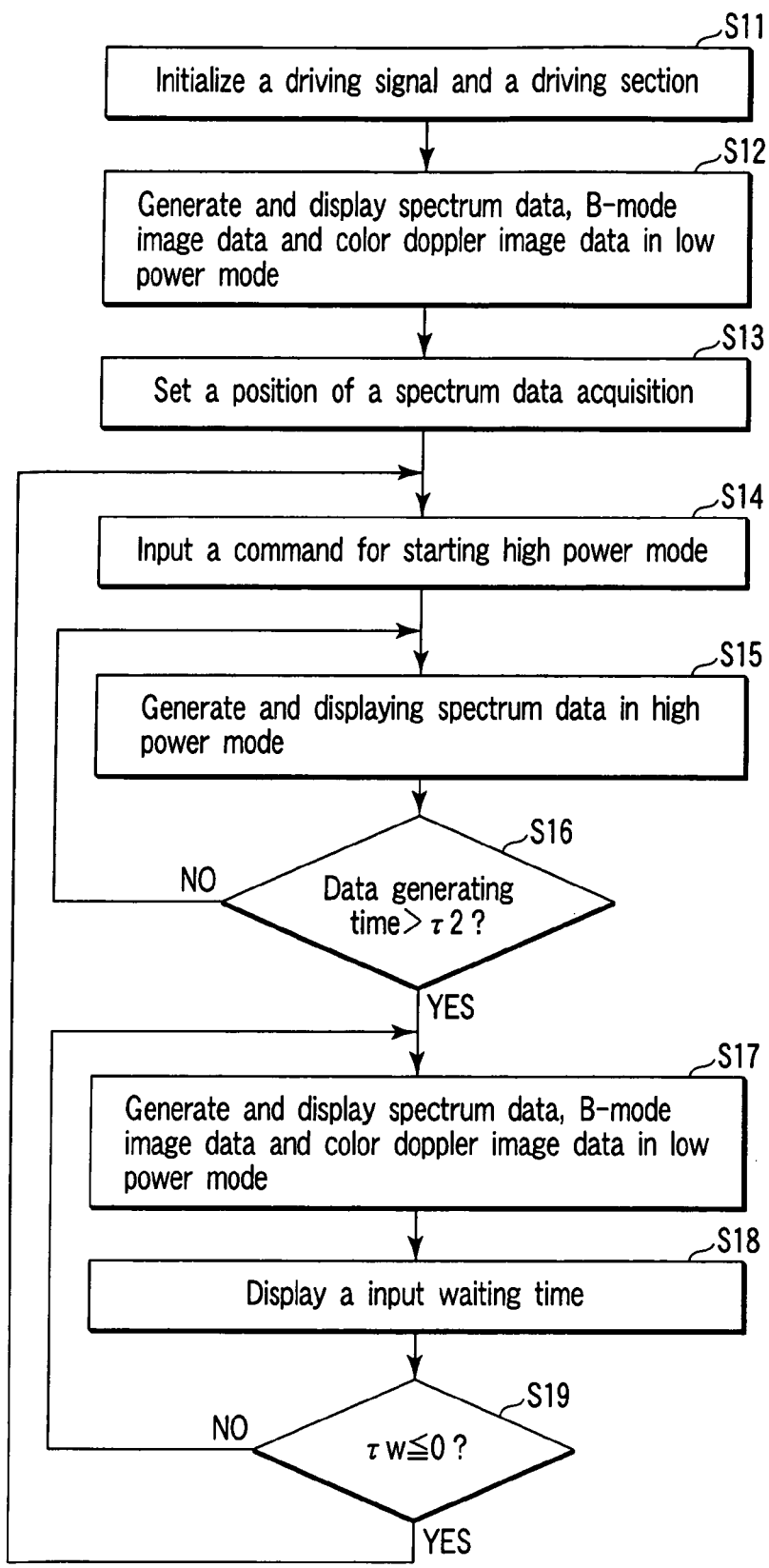
FIG. 13 is a flowchart showing a procedure of generating spectrum data according to a second embodiment of the present invention.

Before collecting ultrasound data, as in the case of the first embodiment, the operator sets a driving voltage, a driving period and the like (step S11 of FIG. 13). For example, by a step similar to the step S7 of FIG. 7, B-mode image data and color Doppler image data of the low-power mode, and spectrum data in a provisional collecting position are generated and displayed (step S12 of FIG. 13).

Next, the operator sets a direction marker and a range gate marker for deciding a collecting position of spectrum data in predetermined positions for the displayed B-mode image data or color Doppler image data (step S13 of FIG. 13). The operator who has observed the displayed spectrum data inputs a driving start command of the high-power mode by desired timing by an input unit 17 (step S14 of FIG. 13).

A system controller 19 that has received the command signal temporarily stops the generation of the B-mode data and the color Doppler data. Then, an acoustic power controller 80 sets a driving voltage $V_H$ of a driving circuit 43. Subsequently, ultrasound wave transmission/reception is carried out in a scanning direction θD to collect spectrum data. By a step similar to the step S5 of FIG. 7, spectrum data of the high-power mode is generated and displayed (step S15 of FIG. 13).

When the ultrasound wave transmission of the high-power mode and the generation period of the spectrum data reach a preset period τ2 (step S16 of FIG. 13), the system controller 19 restores the generation of the B-mode image data and the color image data. Then, the acoustic power controller 80 sets a B-mode driving voltage $V_{BL}$, a color Doppler driving voltage $V_{CL}$ and a pulse Doppler driving voltage $V_L$ of the low-power mode.

Subsequently, B-mode data, color Doppler data and a Doppler spectrum of the low-power mode are generated by a step similar to the step S12 of FIG. 13, and the B-mode image data, the color Doppler image data and the spectrum data that have been obtained are displayed on a monitor of a displaying unit 15 (step S17 of FIG. 13).

Figures 14A, 14B:
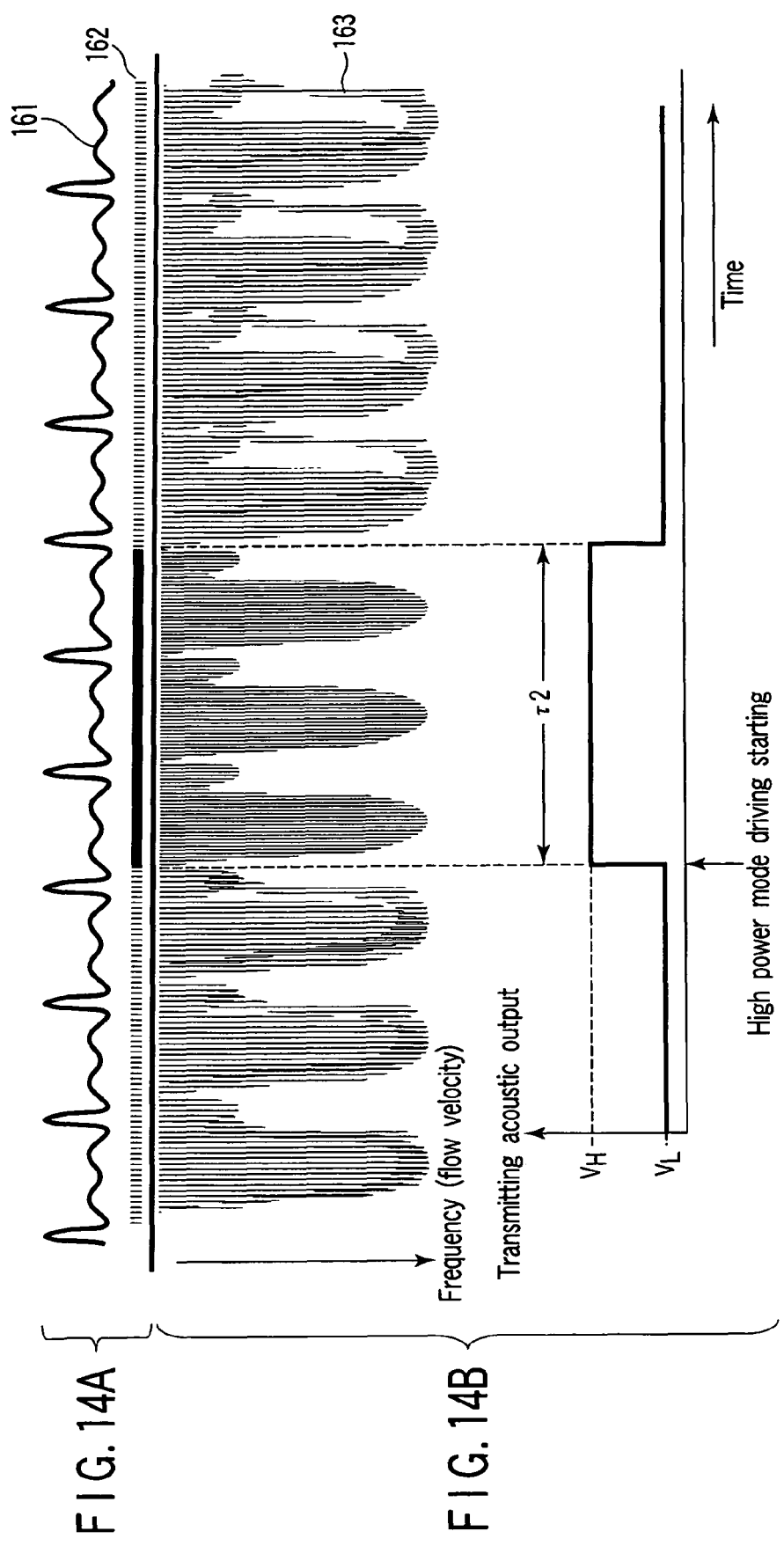
FIGS. 14A and 14B are graphs showing a piezoeletric transducer driving method of the second embodiment and spectrum data obtained by its driving.

FIGS. 14A and 14B show a piezoelectric transducer driving method of the embodiment, and spectrum data obtained by the driving, in which a high-power mode period τ2 is equivalent to roughly three heartbeats of an ECG waveform. According to the embodiment, driving in the high-power mode is carried out based on a driving start command signal which the operator inputs by the input unit 17. Before this driving start command is input, the B-mode image data, the color Doppler image data and the spectrum data of the low-power mode are displayed.

On the other hand, the acoustic power controller 80 pre-calculates a driving period τ3 of the low-power mode by substituting a driving voltage $V_H$ and a driving period τ2 of the high-power mode and a driving voltage $V_L$ of the low-power mode for the equation (1), and calculates an input waiting time τw (τw=τ3−τx) of the driving start command signal based on the data generation period τx and the driving period τ3 of the low-power mode. Then, the input waiting time τw is fed through the system controller 19 and a data processing/storing unit 70 to the display unit 15. The display unit 15 synthesizes information regarding the input waiting time τw with the spectrum data or the like, and displays a result on the monitor (step S18 of FIG. 13).

Figure 15:
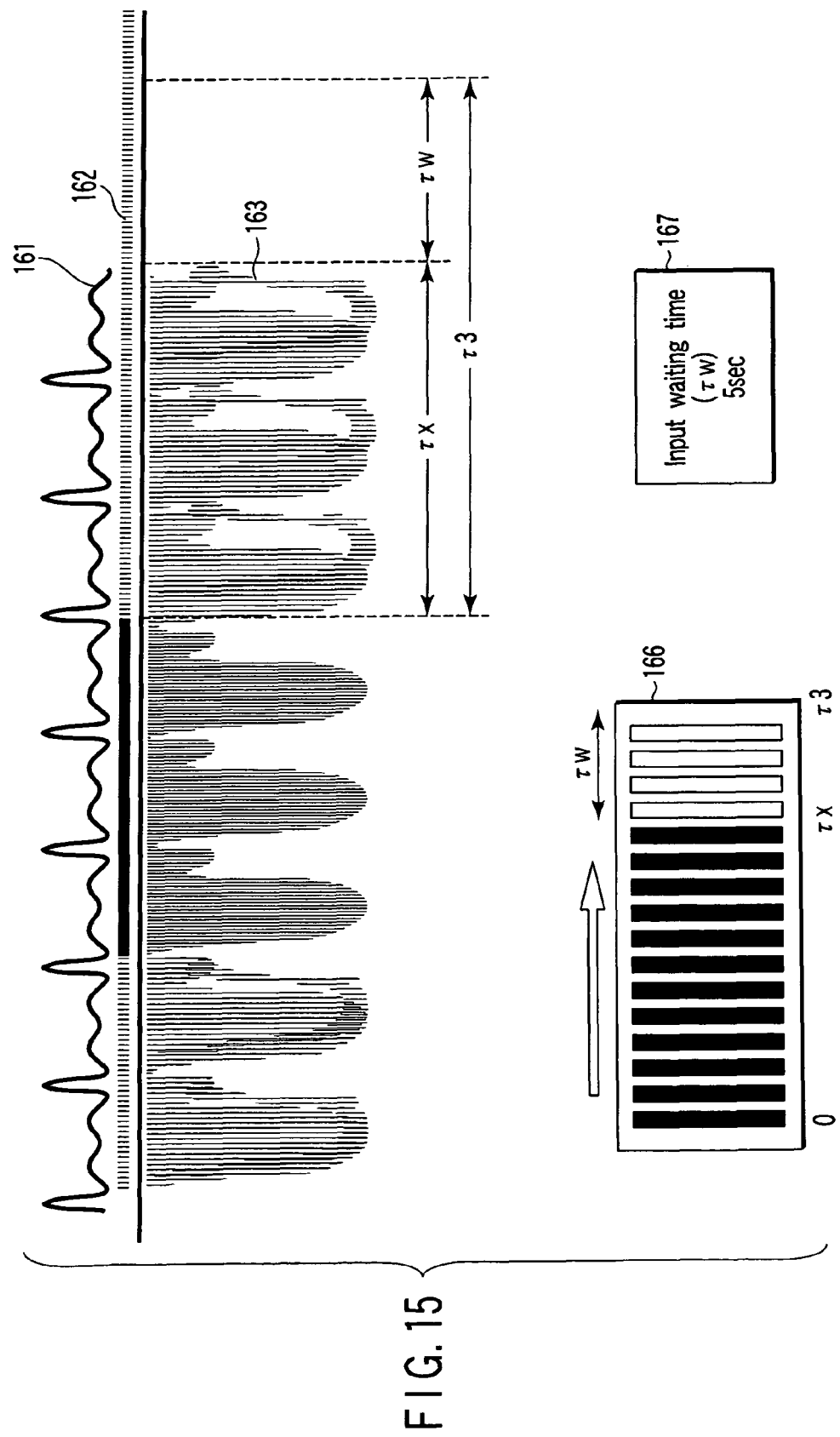
FIG. 15 is a graph showing the spectrum data of the second embodiment and a display example of an input waiting time.
Figure 16:
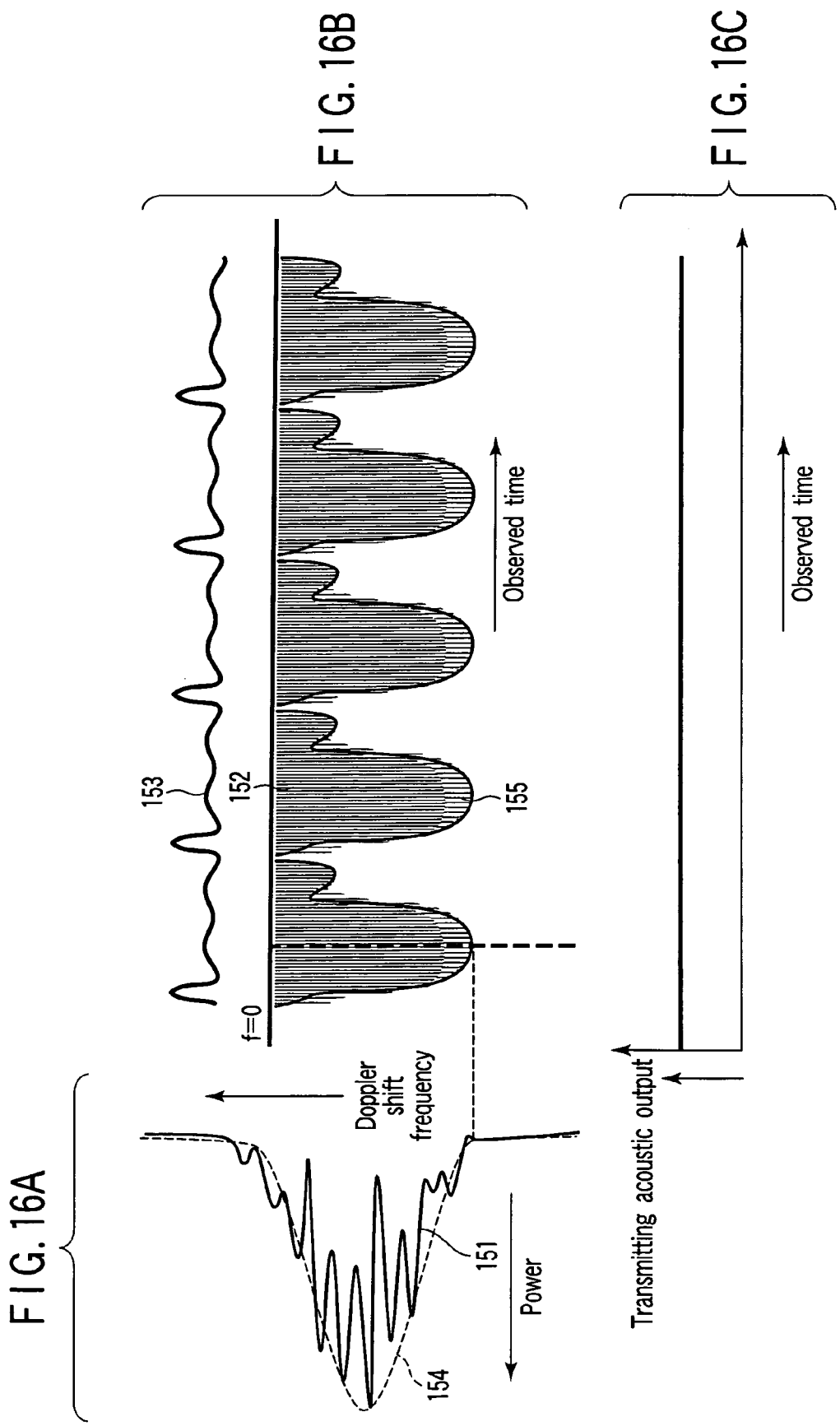
FIGS. 16A to 16C are graphs showing a conventional piezoelectric transducer driving method and spectrum data obtained by its driving.

FIG. 15 shows a display example of the input waiting time, in which together with an ECG wave 161, a high-power indicator 162, and spectrum data 163, a generation time bar indicating latest data of the data generation time τx and a waiting time display section 167 displaying the input waiting time τw are shown. Then, the operator returns to the step S14 of FIG. 13 after confirming that the input waiting time τw has become 0 (step S19 of FIG. 13), and repeats the steps S14 to S19 thereafter.

As described above, according to the second embodiment, as in the case of the first embodiment, the ultrasound wave transmission/reception is carried out by classifying the spectrum data generation period of the ultrasound Doppler spectrum method into the high-power mode period having transmitted acoustic power larger than that of the conventional method and the low-power mode period of transmitted acoustic power smaller than that of the conventional method. Thus, it is possible to generate high-sensitivity spectrum data used for diagnosis in the high-power mode period, and to confirm a normal operation of the apparatus, the data collection position or the like in the low-power mode period. Thus, generation of tracing data for the high-sensitivity spectrum data obtained in the high-power mode period is facilitated, a load on the operator is reduced, and diagnosing efficiency is increased.

The waiting time until the driving start of the high-power mode is displayed based on the permitted transmitted acoustic power set by the heat generation regulations or the acoustic power regulations, the transmitted acoustic power and the driving period of the high-power mode, and the transmitted acoustic power of the low-power mode. The operator can input the driving start command of the high-power mode based on the waiting time. Thus, the established regulations can be complied with, and a clinically required high-sensitivity spectrum or spectrum data can be obtained by desired timing.

The second embodiment has been described by way of the method of displaying the input waiting time in the display unit. However, when the data generation time τx of the low-power mode becomes equal to the preset driving time (continuance time) τ3, this message may be displayed in the display unit, or a voice of a voice output unit (not shown) may be used.

Furthermore, according to the embodiment, when the spectrum data is generated by the continuous Doppler method, high-power mode transmission/reception is carried out by alternately switching a first transducer group and a second transducer group adjacent to the first in the ultrasound probe, whereby it is possible to reduce the amount of generated heat in the ultrasound probe.

The embodiments of the present invention have been described. However, the embodiments are not limitative of the invention. Various changes can be made. For example, to increase the transmitted acoustic power more in the high-power mode, the driving voltage $V_L$ of the low-power mode may be set to 0, i.e., the transmission/reception of the ultrasound waves may be stopped, and similarly the B-mode image data and the color Doppler image data of the low-power mode do not need to be displayed.

The ECG unit used in the embodiments may be incorporated in the ultrasound diagnostic apparatus or independently installed. FIGS. 12A to 12C show the transmission vibration group and the reception vibration group having N/2 piezoelectric transducers. However, the numbers of piezoelectric transducers do not need to be equal between the transducer groups. Moreover, the embodiments have been described by way of the tracing data generation for the maximum frequency component of the spectrum data. However, the invention is not limited to this. For example, tracing data may be generated for an average frequency component or a center frequency component. The heat rate of the ECG waveform included in the high-power and low-power mode periods is not limited to that of the embodiment.

Furthermore, according to the embodiments, the receiver is an analog type. However, it may be a digital type. The B-mode image data and the color Doppler image data generated in the ultrasound diagnostic apparatus are not limited to the two-dimensional image data. They may be three-dimensional image data. Then, for the ultrasound probe, the piezoelectric transducers may be two-dimensionally arrayed to generate three-dimensional image data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An ultrasound diagnostic apparatus comprising:
   an ultrasound probe having a plurality of piezoelectric transducers to transmit ultrasound waves to a subject and to receive echoes from the subject;
   a driving unit configured to generate a plurality of driving signals corresponding to the plurality of piezoelectric transducers to generate the ultrasound waves therefrom;
   a controller configured to control the driving unit to switch, in synchronization with a biomedical signal of the subject, between a high-power mode in which amplitude of the driving signal is relatively high and a low-power mode in which amplitude of the driving signal is relatively low;
   a Doppler signal detecting unit configured to detect Doppler signals based on the echoes;
   a spectrum data generating unit configured to generate spectrum data based on the detected Doppler signals;
   a display unit configured to display the spectrum data and configured to display an electrocardiographic waveform of the subject together with an adjustable line mark corresponding to a continuance period of the high-power mode, wherein the controller initially sets the line mark corresponding to a partial period of a heartbeat cycle of the subject; and
   an operating unit allowing an operator to adjust a position and a length of the line mark, and the controller sets the continuance period of the high-power mode in accordance with the position and the length of the line mark as adjusted by the operator,
   wherein three among four parameters of a driving voltage $V_H$ in the high-power mode, a high-power mode driving period $\tau 2$, a driving voltage $V_L$ in the low-power mode, and a low-power mode driving period $\tau 3$ are set by the operator, and the other parameter not set by the operation is determined in accordance with formula $$K(V_H^2 \tau 2 + V_L^2 \tau 3)/(\tau 2 + \tau 3) < W0$$

in which W0 is an upper limit of transmitted acoustic power permitted per unit time.

2. The ultrasound diagnostic apparatus according to claim 1, wherein the operating unit is further configured to allow individually setting a heart rate in which the high-power mode is continued and a heart rate in which the low-power mode is continued.

3. The ultrasound diagnostic apparatus according to claim 1,
   wherein the driving signal of the high-power mode is larger in voltage amplitude than the driving signal of the low-power mode.

4. The ultrasound diagnostic apparatus according to claim 3,
   wherein the driving signal of the high-power mode is substantially equal in center frequency to the driving signal of the low-power mode.

5. The ultrasound diagnostic apparatus according to claim 1, further comprising a cine-data generating unit configured to generate cine-data by connecting the spectrum data obtained in the high-power mode.

6. The ultrasound diagnostic apparatus according to claim 1,
   wherein the driving unit alternately switches the piezoelectric transducers driven in the high-power mode between first and second piezoelectric transducers of the ultrasound probe for each continuance period of the high-power mode.

7. An ultrasound diagnostic apparatus comprising:
   an ultrasound probe having a plurality of piezoelectric transducers to transmit ultrasound waves to a subject and to receive echoes from the subject;
   a driving unit configured to generate a plurality of driving signals corresponding to the plurality of piezoelectric transducers to scan the inside of the subject with the ultrasound waves;
   a controller configured to control the driving unit to switch, in synchronization with a biomedical signal of the subject, between a high-power mode in which amplitude of the driving signal is relatively high and a low-power mode in which amplitude of the driving signal is relatively low;
   a data image generating unit configured to generate image data based on the echoes;
   a display unit configured to display the image data and configured to display an electrocardiographic waveform of the subject together with an adjustable line mark corresponding to a continuance period of the high-power mode, wherein the controller initially sets the line mark corresponding to a partial period of a heartbeat cycle of the subject; and
   an operating unit allowing an operator to adjust a position and a length of the line mark, and the controller sets the continuance period of the high-power mode in accordance with the position and the length of the line mark as adjusted by the operator,
   wherein three among four parameters of a driving voltage $V_H$ in the high-power mode, a high-power mode driving period $\tau 2$, a driving voltage $V_L$ in the low-power mode, and a low-power mode driving period $\tau 3$ are set by the operator, and the other parameter not set by the operator is determined in accordance with formula $$K(V_H^2 \tau 2 + V_L^2 \tau 3)/(\tau 2 + \tau 3) < W0$$

in which W0 is an upper limit of transmitted acoustic power permitted per unit time.

* * * * *